US012692528B2

(12) United States Patent
    Saito

(10) Patent No.: US 12,692,528 B2
(45) Date of Patent: Jul. 28, 2026

(54) SENSING DEVICE AND METHOD OF DETECTING TARGET SUBSTANCE

(71) Applicant: KABUSHIKI KAISHA TOSHIBA, Tokyo (JP)

(72) Inventor: Tatsuro Saito, Kawasaki (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 499 days.

(21) Appl. No.: 18/184,130

(22) Filed: Mar. 15, 2023

(65) Prior Publication Data

US 2024/0093260 A1    Mar. 21, 2024

(30) Foreign Application Priority Data

Sep. 20, 2022    (JP) ................................. 2022-149614

(51) Int. Cl.
    *C12Q 1/00* (2006.01)
    *G01N 27/414* (2006.01)
    *G01N 33/00* (2006.01)

(52) U.S. Cl.
    CPC ......... *C12Q 1/002* (2013.01); *G01N 27/4145* (2013.01); *G01N 33/0027* (2013.01)

(58) Field of Classification Search
    None
    See application file for complete search history.

(56) References Cited

U.S. PATENT DOCUMENTS

| 2013/0012597 A1 | 1/2013 | Shimada et al. | |
| 2013/0217074 A1* | 8/2013 | Sjoede ..................... | C08H 6/00 |
| | | | 435/162 |

| 2020/0300804 A1 | 9/2020 | Saito et al. | |
| 2020/0407467 A1 | 12/2020 | Larman et al. | |
| 2021/0080416 A1* | 3/2021 | Sugizaki ................. | B01L 3/508 |
| 2021/0080440 A1 | 3/2021 | Sugizaki | |
| 2022/0081702 A1 | 3/2022 | Saito et al. | |
| 2022/0241702 A1 | 8/2022 | Paek | |
| 2023/0174971 A1* | 6/2023 | Young ................... | C12N 15/75 |

FOREIGN PATENT DOCUMENTS

| JP | S58201977 A | * | 11/1983 |
| JP | H01187086 A | | 7/1989 |
| JP | H0965892 A | * | 3/1997 |
| JP | H09107992 A | | 4/1997 |
| JP | H1075780 A | | 3/1998 |
| JP | 2003232793 A | | 8/2003 |
| JP | 3160111 U | | 6/2010 |
| JP | 2020-153783 A | | 9/2020 |
| JP | 2021047037 A | | 3/2021 |
| JP | 2021-148954 A | | 9/2021 |
| JP | 2022-48731 A | | 3/2022 |
| JP | 2022533778 A | | 7/2022 |
| WO | 2011118587 A1 | | 9/2011 |
| WO | 2019171906 A1 | | 9/2019 |

OTHER PUBLICATIONS

Office Action issued on Oct. 21, 2025, in corresponding Japanese Application No. 2022-149614, 8 pages.

* cited by examiner

*Primary Examiner* — Michael A Marcheschi
*Assistant Examiner* — Ashley Lopezlira
(74) *Attorney, Agent, or Firm* — Maier & Maier, PLLC

(57)                ABSTRACT

According to one embodiment, a sensing device includes a component incorporating unit, enzyme-immobilized tank, an enzyme capture tank, a substrate tank and a sensor.

7 Claims, 20 Drawing Sheets

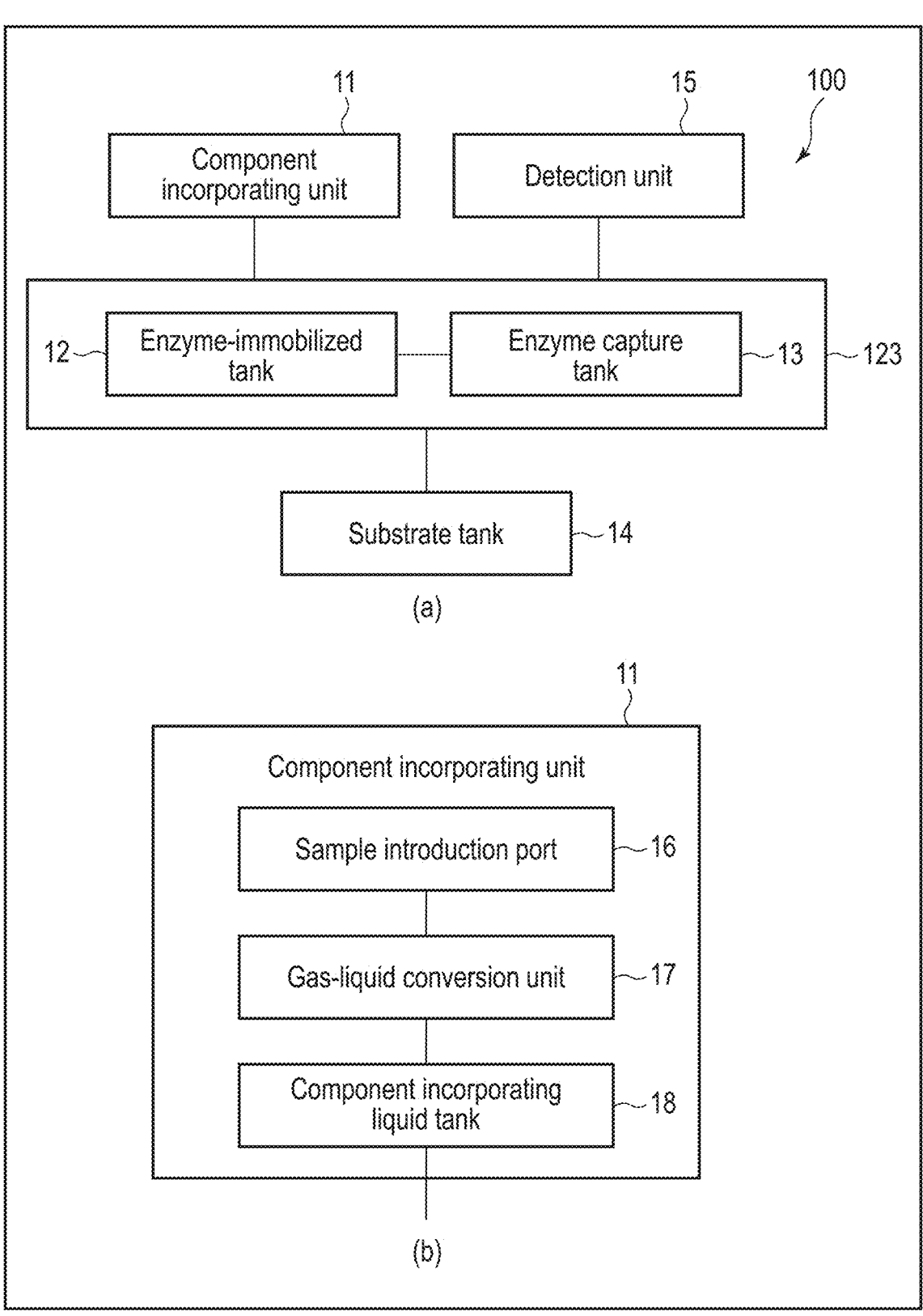
F I G. 1A

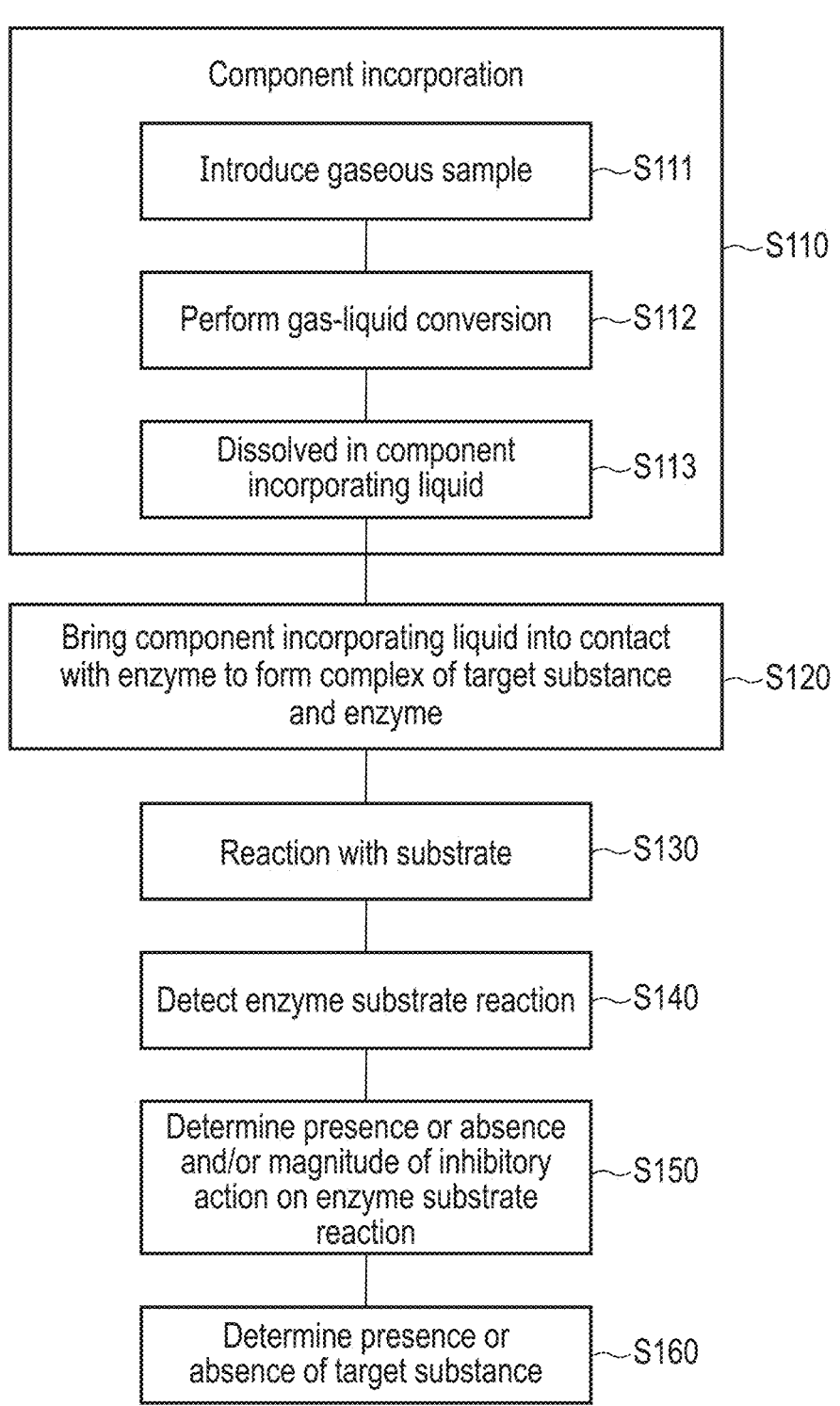
F I G. 1B

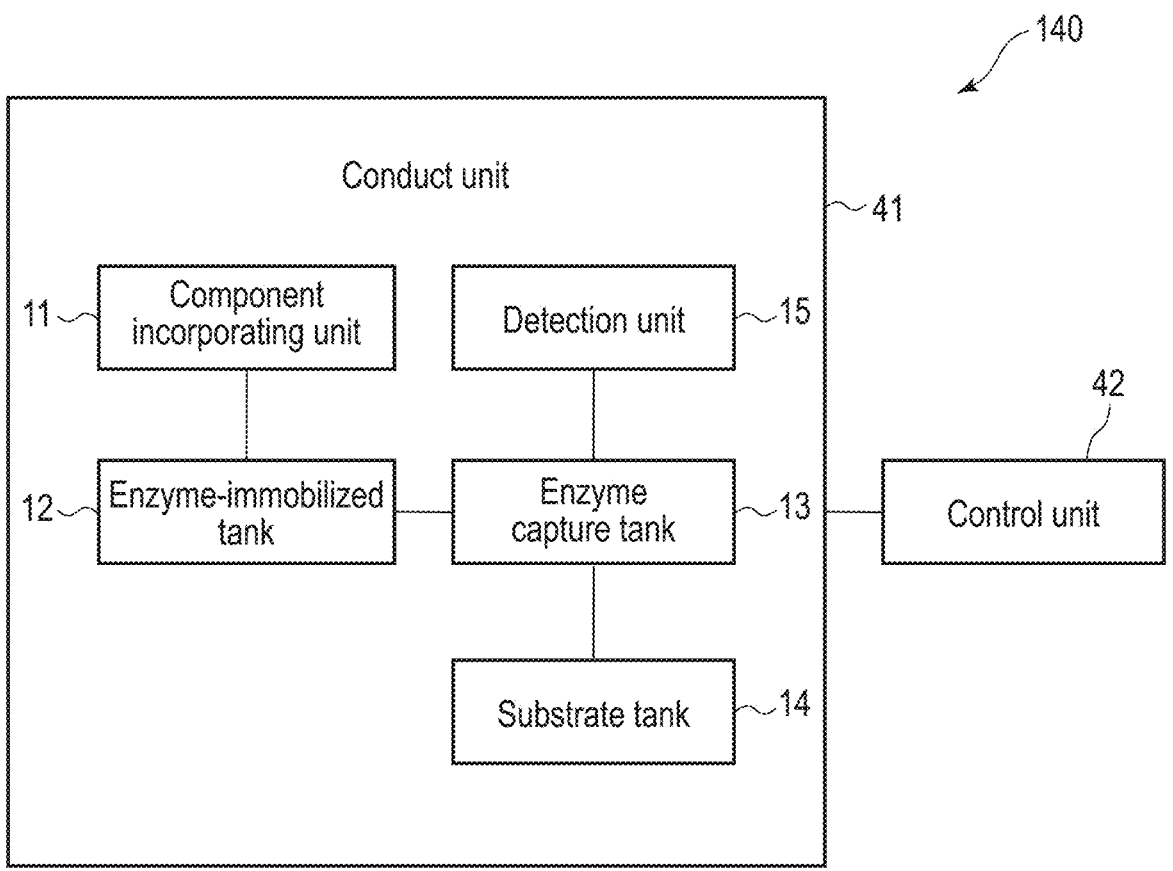
F I G. 4

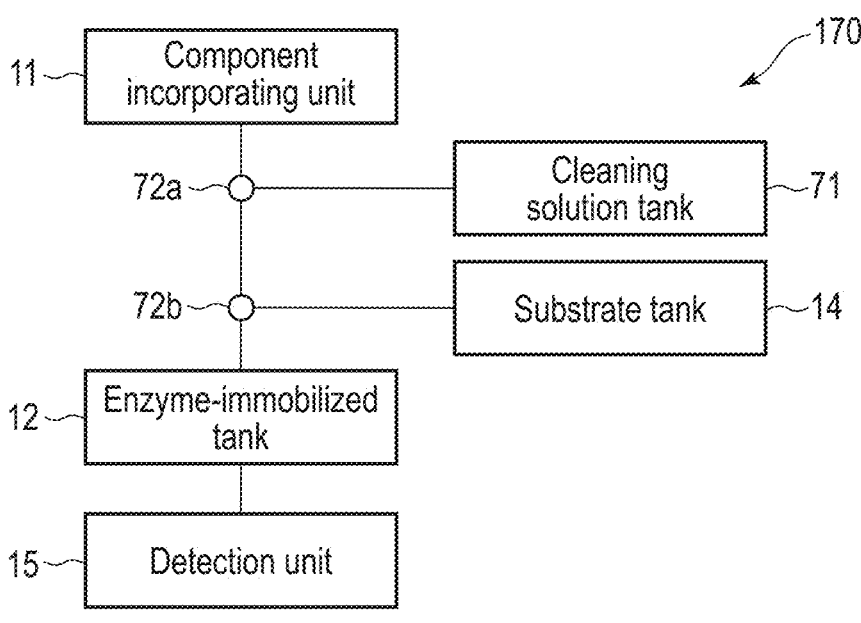
F I G. 7
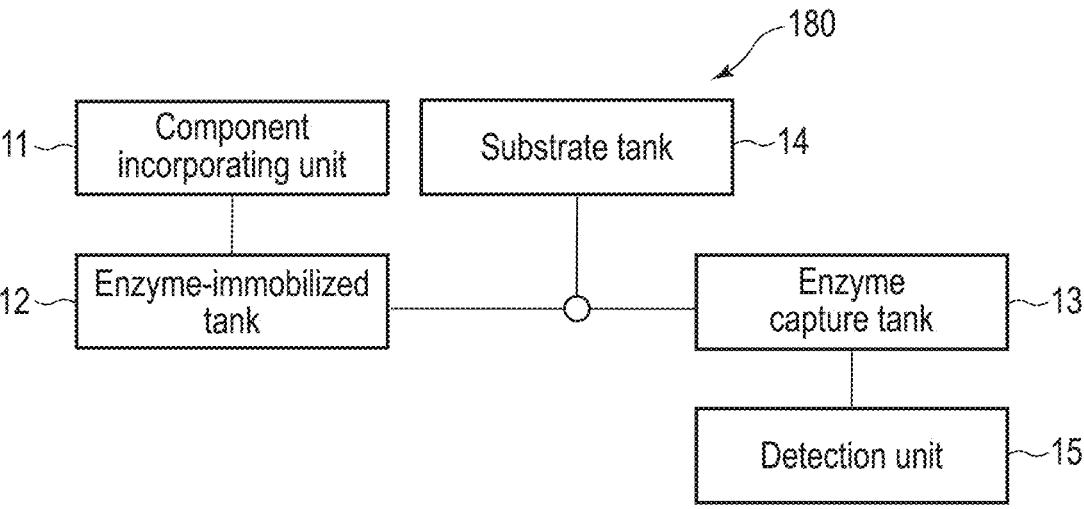
F I G. 8

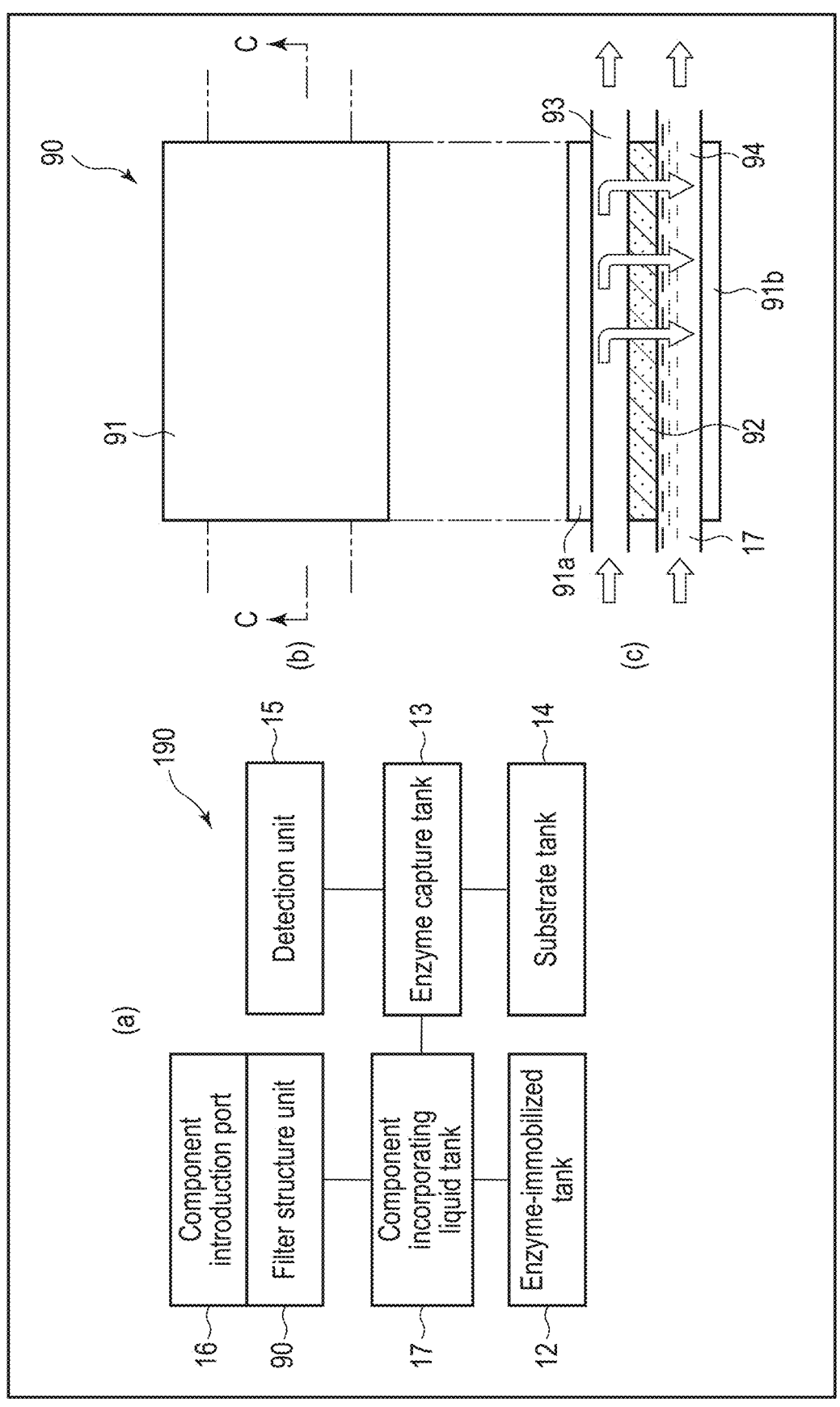
F I G. 9

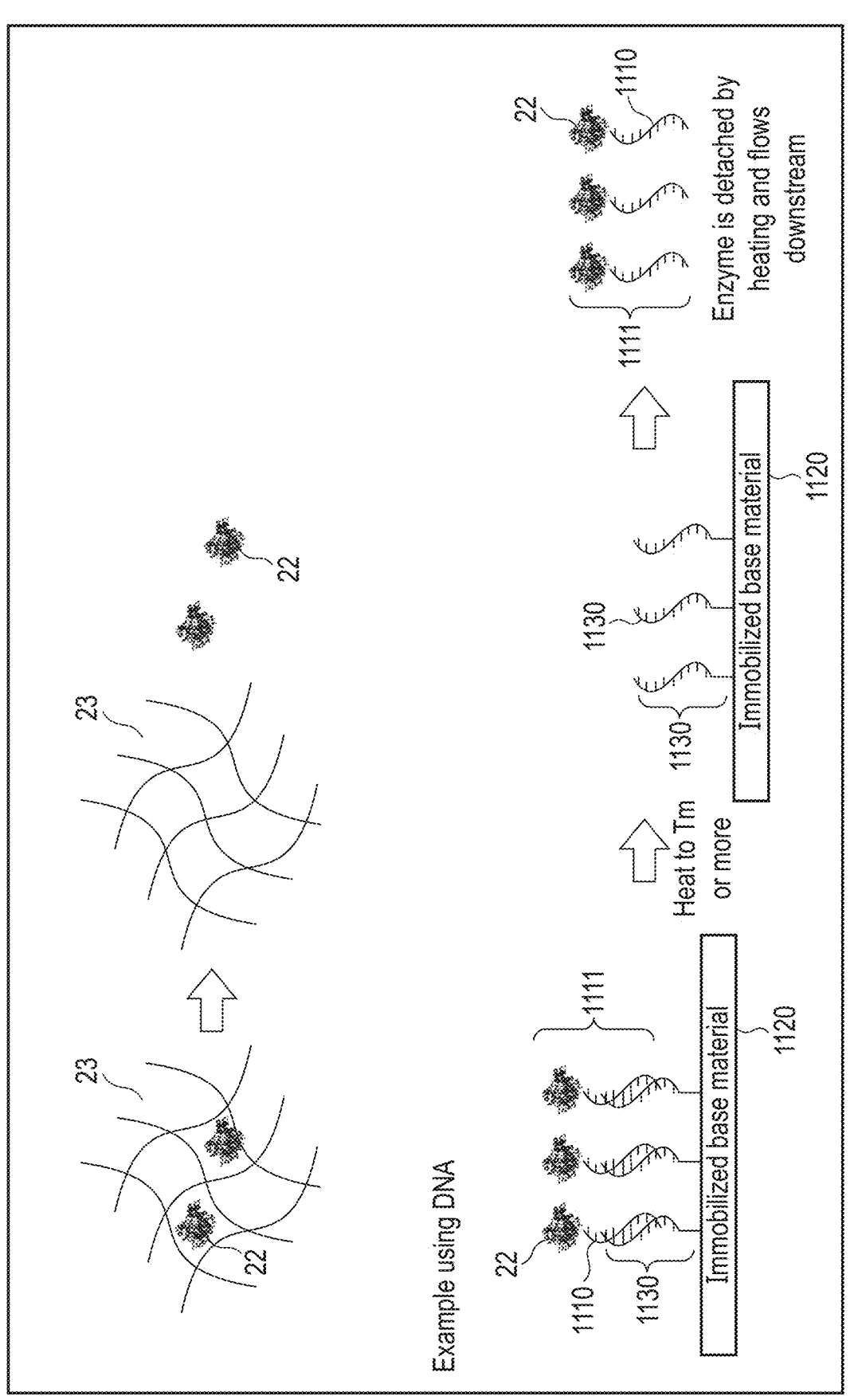
F I G. 11

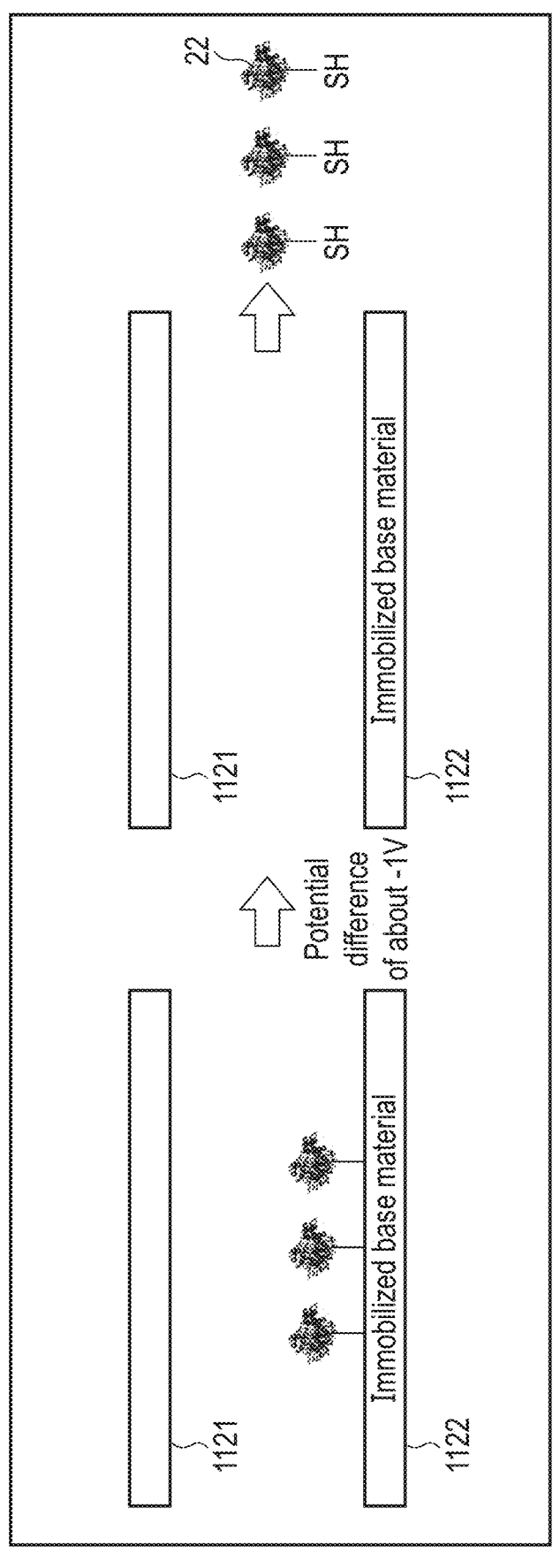
F I G. 12

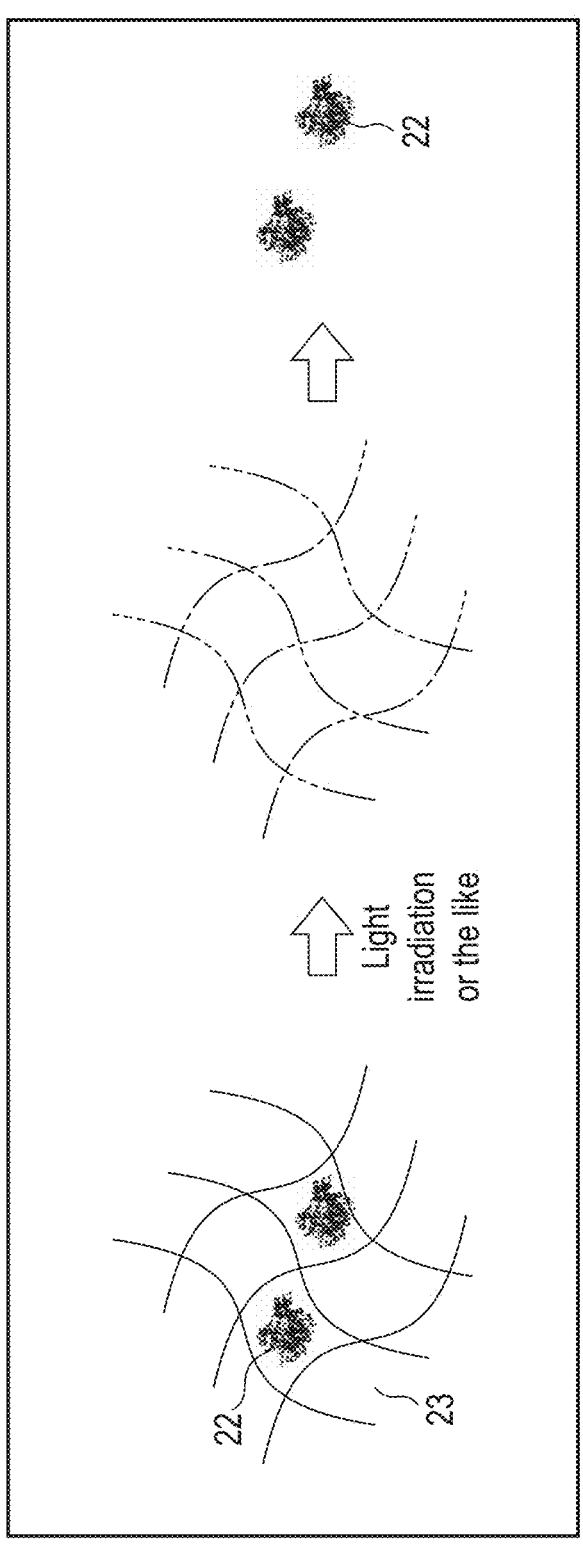
F I G. 13

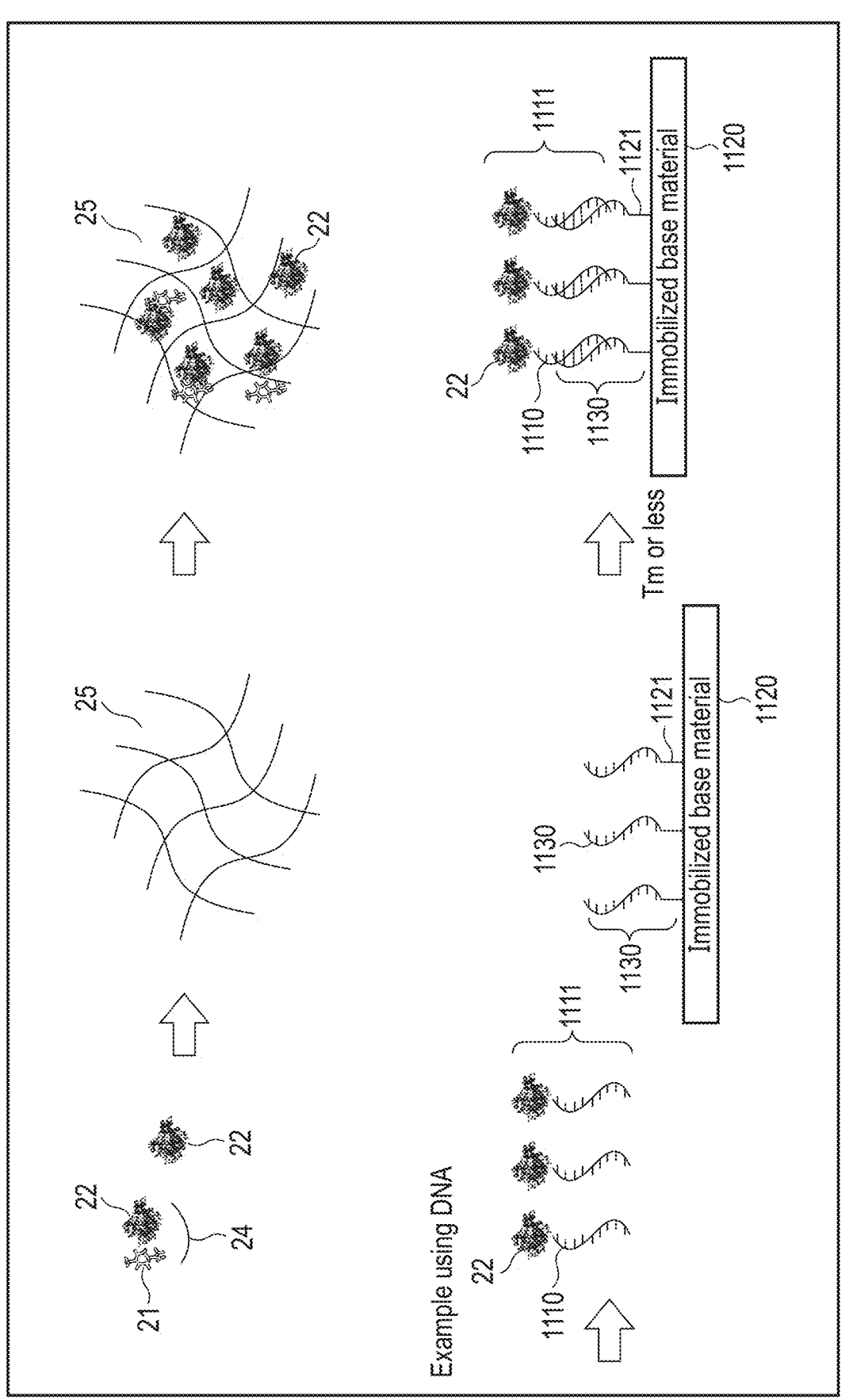
F I G. 14

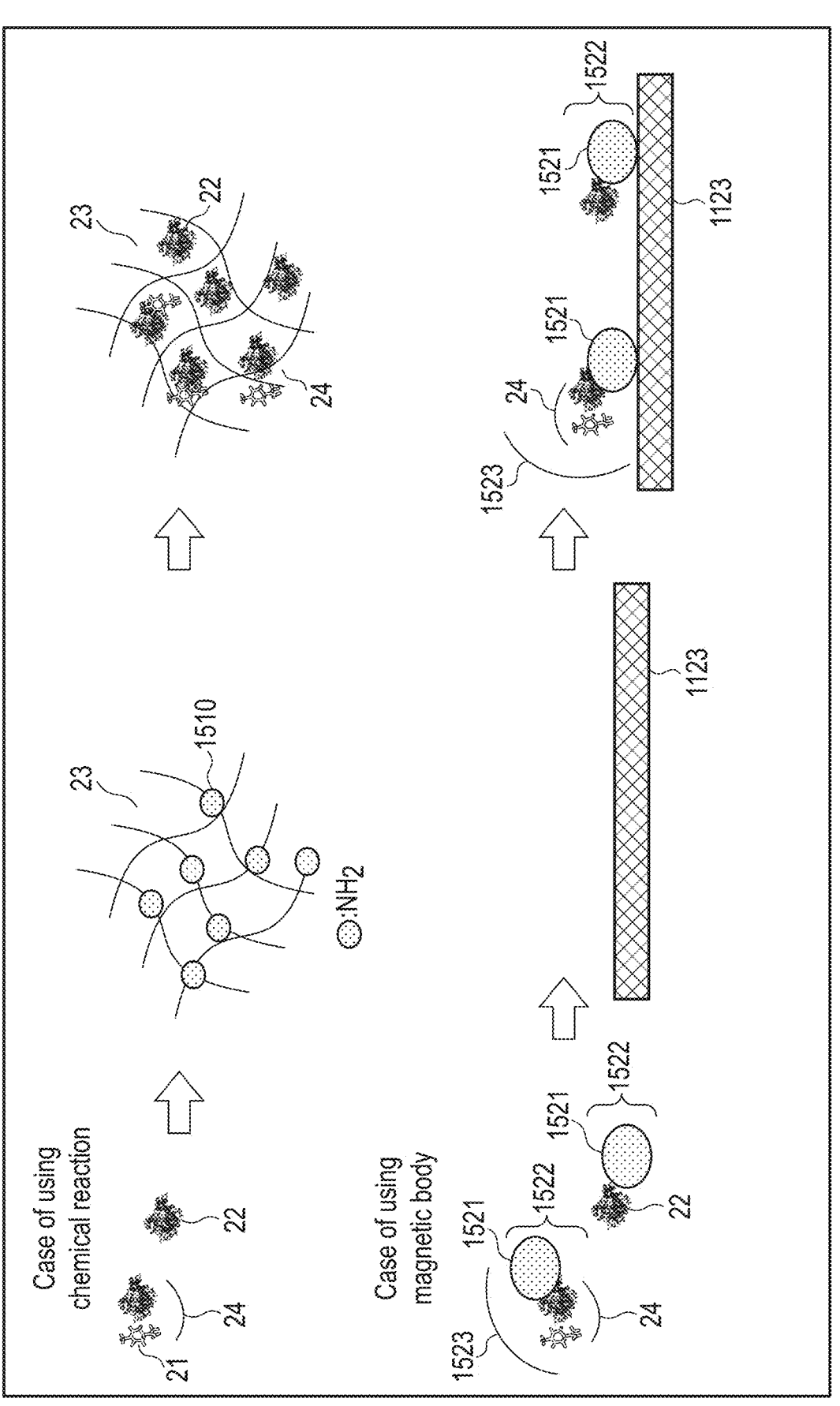
F I G. 15

Table 1. Method of sensitivity improvement

Based on limonene detection mechanism

Inhibition mechanism and reaction rate

Mechanism of reversible inhibition and reaction kinetics

To be obtained is V0 - V1 (corresponding to amount of pH change caused by limonene in case of reflux system).

In case of [E] to [I]

$$\frac{v_i}{v_0} = \frac{([E]+[I]+K_i^{app}) - \sqrt{([E]+[I]+K_i^{app})^2 - 4[E][I]}}{2[E]}$$

Equation of Morrison

Antagonistic inhibition:     $K_i^{app} = K_i\left(1 + \frac{[S]}{K_m}\right)$     (4.16)

Non-antagonistic inhibition:     $K_i^{app} = \dfrac{K_i(K_m + [S])}{\frac{K_m}{K_i} + \frac{[S]}{\alpha K_i}}$     (4.17)     here, when α = 1, $K_i$app = Ki Non-antagonistic inhibition:     $K_i^{app} = K_i\left(1 + \frac{K_m}{[S]}\right)$     (4.18)     Inhibition mode of this time When Kiapp (apparent inhibitor - enzyme binding factor) is high, sensitivity is limited by Kiapp.

It is important to lower Kiapp by lowering [S] (substrate concentration).

Then, it is necessary to lower [E] (enzyme concentration).

FIG. 17

Table 2

Since inhibition model is of non-competition (+ competition), in order to increase sensitivity, it is effective to lower substrate concentration and lower enzyme concentration to cause inhibition event.

Limonene

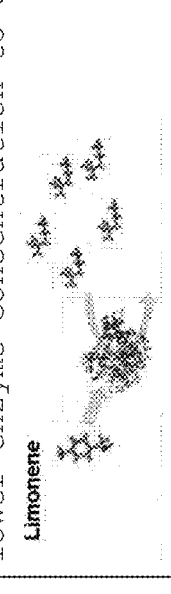

Equilibrium reaction between limonene and ACh

When number of ACh molecules is more than limonene's, inhibition probability decreases (because inhibition does not occur when ACh molecules enter initially).

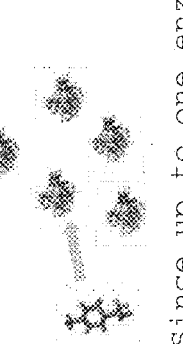

When ACh molecules decrease, probability that limonene molecules enter inhibition pockets increases.

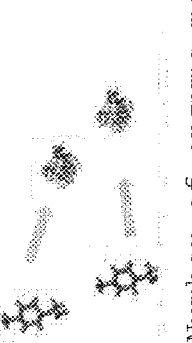

Since up to one enzyme molecule is inactivated by one limonene molecule, it is necessary to reduce number of enzyme molecules when limonene concentration decreases.

Number of enzyme molecules should be reduced, or number of limonene molecules passed should be increased.

Table 3. Feasibility of sensitivity improvement

Considering signal from enzymatic reaction

Maximum signal amount $\propto$ enzyme reaction rate v* time t

Rate equation of enzyme reaction (Michaelis Menten equation)

$$v = \frac{k_1 k_{cat} [E]_0 [S]_0}{k_2 + k_{cat} + k_1 [S]_0}$$

v: rate, [E]: enzyme concentration, [S]: substrate concentration

By lowering [E] and [S], enzyme activity rate changes
with low concentration of inhibitor.

FIG. 19

SENSING DEVICE AND METHOD OF DETECTING TARGET SUBSTANCE

CROSS-REFERENCE TO RELATED APPLICATIONS

This application is based upon and claims the benefit of priority from Japanese Patent Application No. 2022-149614, filed Sep. 20, 2022, the entire contents of which are incorporated herein by reference.

FIELD

Embodiments described herein relate generally to a sensing device and a method for detecting a target substance.

BACKGROUND

A sensor using a reaction between an enzyme and a substrate for detecting a gas component has been proposed.

BRIEF DESCRIPTION OF THE DRAWINGS

FIG. 1A is a block diagram illustrating a first embodiment.

FIG. 1B is a scheme diagram illustrating the first embodiment.

FIG. 4 is a block diagram illustrating a fourth embodiment.

FIG. 7 is a block diagram illustrating a seventh embodiment.

FIG. 8 is a block diagram illustrating an eighth embodiment.

FIG. 9 is a diagram illustrating a ninth embodiment.

FIG. 11 is a schematic diagram illustrating an eleventh embodiment.

FIG. 12 is a schematic diagram illustrating a twelfth embodiment.

FIG. 13 is a schematic diagram illustrating a thirteenth embodiment.

FIG. 14 is a schematic diagram illustrating a fourteenth embodiment.

FIG. 15 is a schematic diagram illustrating a fifteenth embodiment.

FIG. 17 is a table showing a method of sensitivity improvement.

FIGS. 18A-18B are tables showing technical ideas of the sensing device of the first embodiment.

FIG. 19 is a table showing a reaction rate of an enzymatic reaction without consideration of inhibitors.

DETAILED DESCRIPTION

Figure 2:
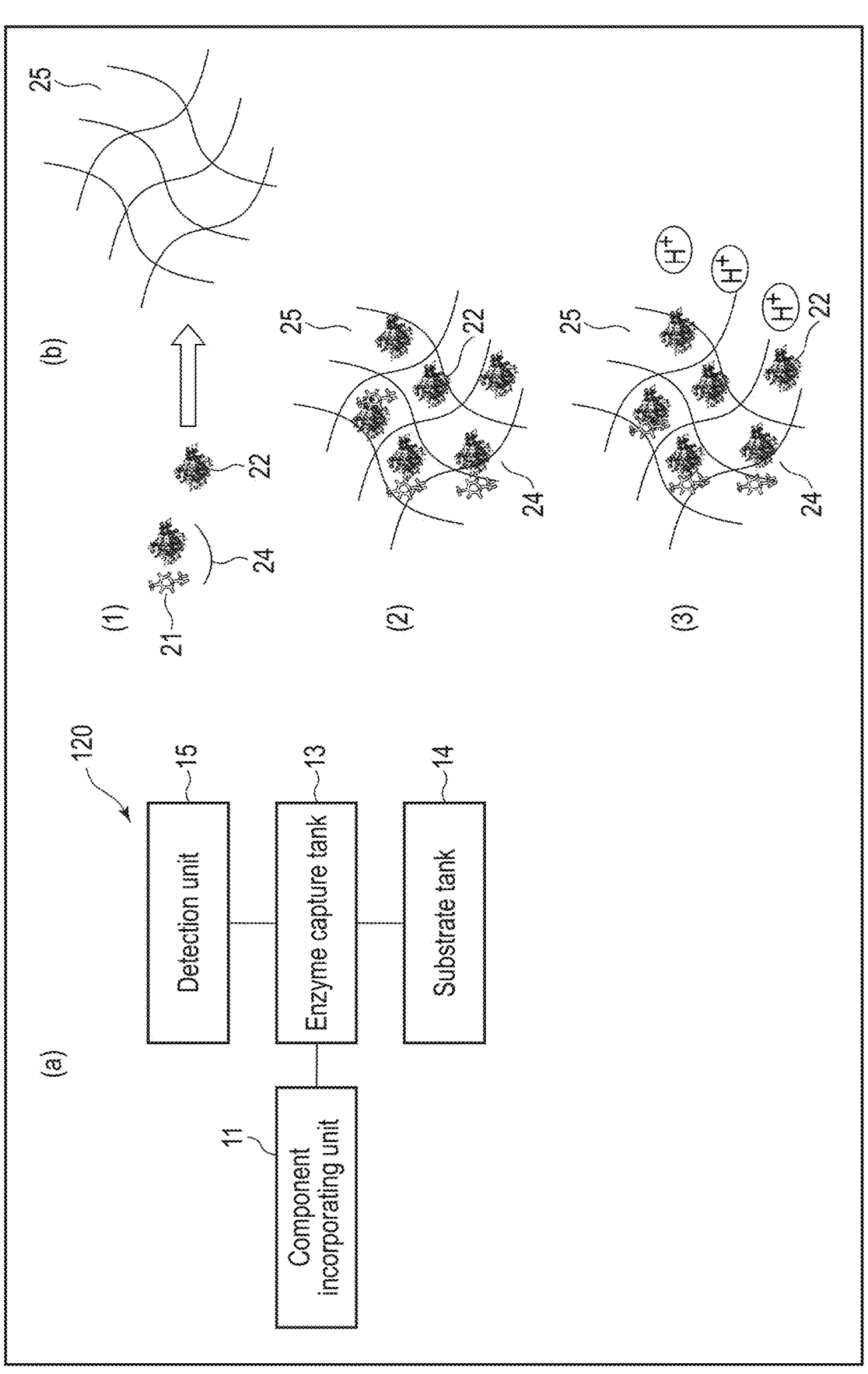
FIG. 2 is a diagram illustrating a second embodiment.

In general, according to one embodiment, a sensing device includes a component incorporating unit, enzyme-immobilized tank, an enzyme capture tank, a substrate tank and a sensor. The component incorporating unit incorporates a sample or at least a part of a component of the sample into a liquid. The an enzyme-immobilized tank liquid-entangles with the component incorporating unit, and the enzyme-immobilized tank includes a support. The support has an enzyme and the enzyme is detachably immobilized on the support. Activity of the enzyme is inhibited by binding of a target substance. The enzyme capture tank captures the enzyme detached from the enzyme-immobilized tank. The substrate tank supplies a substrate solution to the enzyme capture tank. The sensor measures an amount of a substrate or an amount of a product contained in the substrate solution supplied to the enzyme capture tank.

In general, according to one embodiment, an object is to provide a sensing device to more sensitively detect a target substance and a method of detecting a target substance.

First Embodiment

A first embodiment will be described with reference to FIG. 1A. A sensing device 100 of the first embodiment is a sensor for detecting a detection target substance, that is, a target substance, in a sample. As illustrated in FIG. 1A (a), the sensing device 100 includes a component incorporating unit 11, a signal conversion unit 123, a detection unit 15, and a substrate tank 14 that accommodates a substrate. The signal conversion unit 123 includes an enzyme-immobilized tank 12 and an enzyme capture tank 13. The enzyme-immobilized tank 12 includes a support and an enzyme detachably immobilized on the support (not illustrated). When the enzyme comes into contact with the substrate sent from the substrate tank 14, the enzyme exhibits enzyme activity and generates a reaction product. The detection unit 15 senses this enzyme activity. The target substance is an inhibitor against the enzyme, and binds to the enzyme to reversibly and competitively or non-competitively inhibit the enzyme activity of the enzyme, for example, allosterically. The target substance may specifically or non-specifically bind to the enzyme. For example, the sensing of the enzyme activity in the detection unit 15 can be performed by measuring a substrate amount or a reaction product amount.

The sample or at least a part of a component thereof introduced into the sensing device 100 through the component incorporating unit 11 comes into contact with the enzyme in the enzyme-immobilized tank 12. In this case, when the target substance is contained in the sample, a complex of the enzyme-target substance is formed in the enzyme-immobilized tank 12. Next, the enzyme and the complex are detached from the support and sent to the enzyme capture tank 13. The substrate is sent from the substrate tank 14, the reaction between the enzyme and the substrate is performed, and a product (reaction product) is formed. Meanwhile, the complex formed when the target substance is present in the sample inhibits the reaction between the enzyme and the substrate, thereby inhibiting the enzyme activity. The detection unit 15 can measure the enzyme activity of the enzyme by detecting or monitoring the reaction product generated by the reaction between the enzyme and the substrate or the substrate, and can detect the target substance in the sample by decreasing the measured enzyme activity. For example, the detection unit 15 detects the enzyme activity by measuring the substrate amount or product amount (in other words, the reaction product amount) contained in a substrate solution in contact with the enzyme. Detecting the amount of the substrate and/or the product by the detection unit 15 is synonymous with detecting a concentration of the substrate and/or the product in the substrate solution in contact with the enzyme. The enzyme activity can be regarded as an amount of decrease in substrate or an amount of increase in product per reaction time.

Such a configuration can be realized as a sensing device capable of achieving both high sensitivity and high signal by preparing the concentration of the enzyme particularly at the stage of complex formation between the target substance (that is, the inhibitor) and the enzyme or the stage of evaluation of the enzyme activity, as an inhibitor recognition sensor in which non-competitive inhibition and competitive inhibitory action, which are reversible inhibition of the enzyme, are applied to detection. The enzyme-immobilized tank 12 and the enzyme capture tank 13 have carriers such as beads, gels, and polymers modified to be able to bind to the enzyme. The enzyme-immobilized tank 12 and the enzyme capture tank 13 have containers configured to allow various liquids to pass through the carriers. The enzyme-immobilized tank 12 and the enzyme capture tank 13 are, for example, gel packed columns or bead packed columns. The volume of the container of the enzyme-immobilized tank 12 is larger than the volume of the enzyme capture tank 13. The volume of the container of the enzyme-immobilized tank 12 is, for example, 2 times to 500 times the volume of the enzyme capture tank 13. The amount of liquid that can fill the enzyme-immobilized tank 12 is larger than the amount of liquid that can fill the enzyme capture tank 13. The simple substance contained in the enzyme-immobilized tank 12 can include, for example, a support and modifications present on the surface thereof. The simple substance contained in the enzyme capture tank 13 is also referred to as, for example, a capture unit.

The sensing device 100 will be described in more detail. The sample to be sensed in the sensing device 100 may be, for example, a gas or a liquid. When the sample is a gas, as illustrated in FIG. 1A (b), the component incorporating unit 11 include a gas introduction port 16, a gas-liquid conversion unit 17, and a component incorporating liquid tank 18. The sample introduction port 16 is an opening for bringing a sample into the sensing device 100. For example, the opening may be opened widely or in any size, and the gas may be directly recovered from a sample collection atmosphere. The recovery may be either active or passive. Alternatively, for example, a gas sample is collected as a sample in a cylinder with a needle, and is carried from the sample introduction port to the sensing device 100 using the needle attached to the cylinder. The gas sample is brought into contact with the component incorporating liquid in the gas-liquid conversion unit 17, and at least a part of the component including the target substance is incorporated in the take-in liquid and sent to the enzyme-immobilized tank 12. Here, the component incorporating liquid is sent from the component incorporating liquid tank 18 to the gas-liquid conversion unit 17.

When the sample is a liquid, the component incorporating unit 11 includes the sample introduction port 16. The sample inserted from the sample introduction port 16 passes through a flow path (not illustrated) and is sent to the enzyme-immobilized tank 12. In this case, the inserted sample may be mixed with the component incorporating liquid, and for example, at least a part of the component of the liquid sample may be incorporated into the component incorporating liquid and sent to the enzyme-immobilized tank 12 via the gas-liquid conversion unit (not illustrated).

For example, an example of a procedure for detecting a target substance by the sensing device 100 for a gaseous sample will be described with reference to FIG. 1B. The gaseous sample is introduced from the sample introduction port 16 (S111). The introduced gaseous sample comes into contact with the component incorporating liquid in the gas-liquid conversion unit 17, and at least a part of the component of the sample containing the target substance is dissolved and incorporated into the liquid (S113). The liquid is sent to the enzyme-immobilized tank 12, and comes into contact with the enzyme detachably immobilized on the support therein to form an enzyme-target substance complex (S120). Next, the immobilized enzyme and complex are detached and sent to the enzyme capture tank 13. The enzyme and the complex captured by the enzyme capture tank 13 come into contact with the substrate solution from the substrate tank 14 under the sensing by the detection unit 15 (S130). The detection unit 15 detects the reaction between the enzyme and the substrate (S140). For example, the presence or absence and magnitude of the inhibitory action on the enzyme substrate reaction are determined by a calculation unit (not illustrated) such as a computer (S150). The presence or absence of the target substance is determined based on the determination result in S150 (160). The result may be expressed by, for example, display on a display unit (not illustrated) such as a display, sound production such as a buzzer, a bell, or a melody, vibration by a vibrator, or the like.

In particular, in the inhibitor recognition sensor in which the non-competitive inhibition and competitive inhibitory action, which are the reversible inhibition of the enzyme, the concentration of the enzyme is changed in complex formation between a detection target (inhibitor) and the enzyme and evaluation of the enzyme activity. Focusing on changing of the concentration of the enzyme to detection is characteristic. In an enzyme sensor that realizes known inhibitor detection, a structure in which an enzyme is immobilized has been reported. However, in this structure, the concentration of the enzyme is always constant, and thus, the sensitivity and the signal amount are limited. However, in the present embodiment, it is possible to provide a sensor that achieves both high sensitivity and high signal by a structure that realizes change of the enzyme concentration.

Such a sensing device that achieves both high sensitivity and high signal is based on the following technical ideas illustrated in FIGS. 17-19.

In FIGS. 17-19, a notation [ ] means a concentration of an item in the [ ], and a notation [ ] 0 means an initial concentration of the item. E is an enzyme, S is a substrate, ES is an enzyme-substrate complex, I is an inhibitor, EI is an enzyme-inhibitor complex, P is a product, and k is a reaction rate constant. Km is a Michaelis constant, Ki is an inhibition constant (a dissociation constant of EI), and Kiapp notation indicates an apparent dissociation constant. Vi is a reaction rate in the presence of the inhibitor, and V0 is a reaction rate in the absence of the inhibitor.

That is, considering the inhibition mechanism of enzyme activity by a reversible inhibitor such as limonene and the reaction kinetics, V0-Vi should be obtained. When the reaction time is the same, V0 is the amount of change in the substrate or the product in the absence of the inhibitor, and Vi is the amount of change in the substrate or the product in the presence of the inhibitor. Note that V0 may be regarded as a constant, and the inhibitor may be detected by the value of Vi. This corresponds to an amount of pH change caused by limonene in the case of a reflux system. Therefore, an equation of MORRISON illustrated in FIG. 17 is obtained, from which an equation of antagonistic inhibition (4.16), an equation of non-antagonistic inhibition (4.17), and an equation of non-antagonistic inhibition (4.18) are derived. Here, in the present embodiment, the equation of antagonistic inhibition (4.16) and the equation of non-antagonistic inhibition (4.17) are inhibition modes to be used. From this equation, when Kiapp is high, the sensitivity is limited by Kiapp. That is, it is found that it is important to lower Kiapp by lowering [S] (substrate concentration). In addition, it is found that it is necessary to lower [E] (enzyme concentration).

Figure 18B:
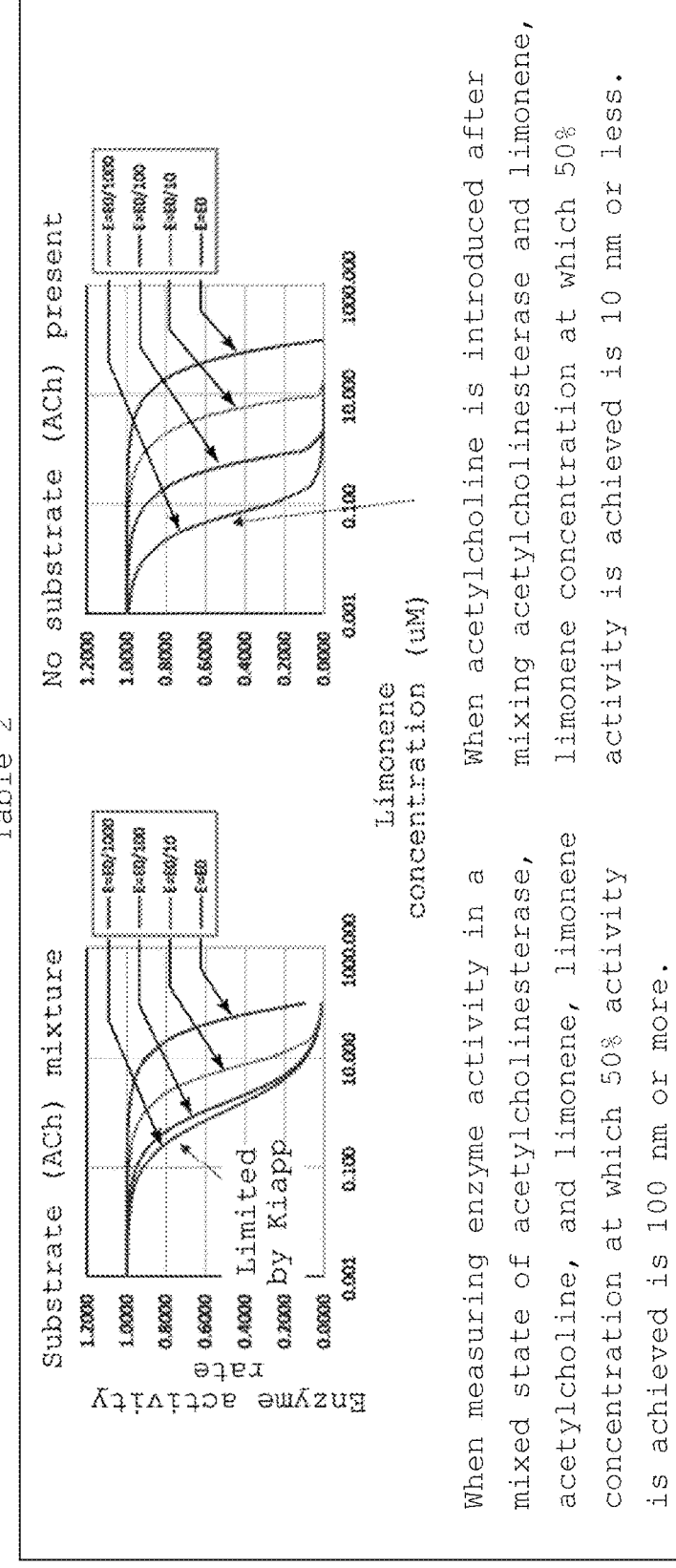

As illustrated in FIGS. 18A-18B, in the case of the sensing device according to the present embodiment, when the detection target is limonene, the inhibition model is non-competition, but it is possible to sufficiently cope with the detection target other than limonene by similarly changing the enzyme to the other proper enzyme for the target. Given the mode of inhibition, it is possible to apply competition in addition to non-competition as the same inhibition model.

In FIGS. 18A-18B, acetylcholinesterase is the enzyme, limonene is the inhibitor, acetylcholine (Ach) and water are the substrates, and choline and acetic acid (acetate ion and hydrogen ion) are the products.

Here, in order to increase the detection sensitivity of the inhibitor, when A is detected, it is found that it is effective to lower the substrate concentration, lower the enzyme concentration, and cause an inhibition event at the time of contact between limonene and the enzyme. Hereinafter, a case where a reaction solution of the enzyme is an aqueous solvent and the inhibitor is a hydrophobic substance such as limonene will be examined. Since limonene is a hydrophobic substance, it cannot be dissolved in a large amount in an aqueous solvent in a free state. In a case where a limonene concentration cannot be sufficiently increased, in the competition between limonene and acetylcholine, when acetylcholine (ACH) first comes into contact with acetylcholinesterase, it is difficult to obtain the inhibitory effect by limonene.

When acetylcholine is present in excess of limonene in the high concentration substrate solution, the probability of inhibition by limonene decreases. The reaction rate does not change regardless of the presence or absence of the inhibitor, and the detection sensitivity of the inhibitor deteriorates.

On the contrary, as the amount of acetylcholine decreases in the field of the reaction, the probability that the inhibitor of the detection target, such as limonene, will enter the inhibition pocket of the enzyme increases. In addition, since up to one enzyme is inactivated by one limonene, it is also necessary to reduce the number of enzymes when the limonene concentration decreases. From this, it is considered that it is also effective to reduce the number of enzymes and increase the number of passed limonene.

Therefore, what is derived from these estimations is that when the inhibitor forms a complex with the enzyme, (1) the amount of substrate is small, and (2) the amount of enzyme is small, so that high sensitivity can be realized.

FIG. 19 illustrates the reaction rate of the enzymatic reaction without consideration of inhibitors. In the reaction between the enzyme and the substrate, it is preferable that the enzyme concentration and the substrate concentration are high in order to increase the reaction rate. The detection accuracy of the inhibitor correlates with the amount of change in the concentration of the substrate or the product in the presence of the inhibitor. When the amount of change in the substrate or the product is large, the detection unit outputs a large signal, and the accurate amount of the inhibitor and the change thereof can be detected. When acetylcholine is present in a large amount in the reaction field between the enzyme and the substrate, a large amount of substrate can be brought to react. The detection unit such as a chemical sensor measures the concentrations of the substrate and the product from the obtained signal, and further multiplies the given solution amount by the concentration to calculate the substrate amount. Even when large amounts of the product and the substrate are present, the product and the substrate cannot be detected unless the concentration is sufficiently detectable by the detection unit 15.

The sensing device 100 of the embodiment forms the complex of the enzyme and the inhibitor which the detection target under conditions of low enzyme concentration and low substrate concentration in the enzyme-immobilized tank 12, and reliably forms an enzyme-inhibitor complex. The sensing device 100 captures and concentrates the enzyme and the enzyme-inhibitor complex, which were separated from the enzyme-immobilized tank 12, in the enzyme capture tank 13 having a volume smaller than that of the enzyme-immobilized tank 12, and performs the enzyme substrate reaction at a high enzyme concentration and a high substrate concentration. The detection unit 15 can detect that the inhibitor is contained in the sample and the content of the inhibitor from the change in the amount or concentration of the high-concentration substrate and product. Even when the amount and concentration of the inhibitor contained in the sample or the incorporating solution are low, the sensing device 100 of the embodiment can detect the inhibitor with high sensitivity because the signal of the enzyme/product amount is amplified by the enzymatic reaction. The sensing device 100 of the embodiment can achieve both detection sensitivity and detection accuracy.

In such a sensor, it is possible to detect whether or not the target component (here, it can also be referred to as a detection target substance or a target substance) is mixed in the gas or the liquid incorporated into a sample incorporating unit by measuring molecules or ions generated by the enzymatic reaction in the signal conversion unit by the detection unit.

Second Embodiment

A second embodiment will be described with reference to FIG. 2. As illustrated in FIG. 2(*a*), a sensing device 120 includes a component incorporating unit 11, an enzyme capture tank 13 connected thereto, a substrate tank 14 that supplies a substrate solution to the enzyme capture tank 13, and a detection unit 15 that senses a reaction product generated by a reaction between an enzyme and a substrate.

In the case of the sensing device 120, a detection target substance 21 from the incorporated sample and an enzyme 22 are brought into contact with each other after the sample or at least a part of the component of the sample is incorporated by the component incorporating unit 11 (FIG. 2(*b*)(1)). The enzyme 22 is included in, for example, a component incorporating solution. By the contact, the target substance 21 and the enzyme 22 form a complex 24. Both the complex 24 and the enzyme 22 having no complex formed are sent to the enzyme capture tank 13 and captured by a capture unit 25 placed in the enzyme capture tank 13 (FIG. 2(*b*)(2)). A substrate solution is supplied from the substrate tank 14 to the complex 24 and the enzyme 22 immobilized on the capture unit 25, and the enzyme 22 reacts with the substrate to generate, for example, $H^+$ as a reaction product. The detection unit 15 monitors the occurrence of $H^+$. Meanwhile, the reaction of the enzyme present as the complex 24 with the substrate is inhibited by the presence of the target substance 21. Therefore, a production amount of H$^+$ is smaller than that in a case where the target substance 21 is not present. Thus, sensing of the target substance 21 is achieved.

The sensor of the detection unit 15 can be configured to also function as a capture unit of the enzyme capture tank 13. The capture unit 25 may be formed from conductive paper, for example, a nonwoven fabric or a cellulose material, particles, for example, gold nanoparticles or polymer particles, a porous structure, for example, porous glass or ceramics, or the like.

By performing the formation of the complex 24 and the sensing by the detection unit 15 in a state of being captured by the enzyme capture tank 13 in a stepwise manner, and performing sensing in a state of being immobilized on the enzyme capture tank 13, that is, in a state of having a low enzyme density, it is possible to detect a trace amount of target substance with higher sensitivity. That is, by efficiently generating an enzyme-target substance complex in a state where the enzyme and the substrate concentration are low, high sensitivity can be realized.

Third Embodiment

Figure 3:
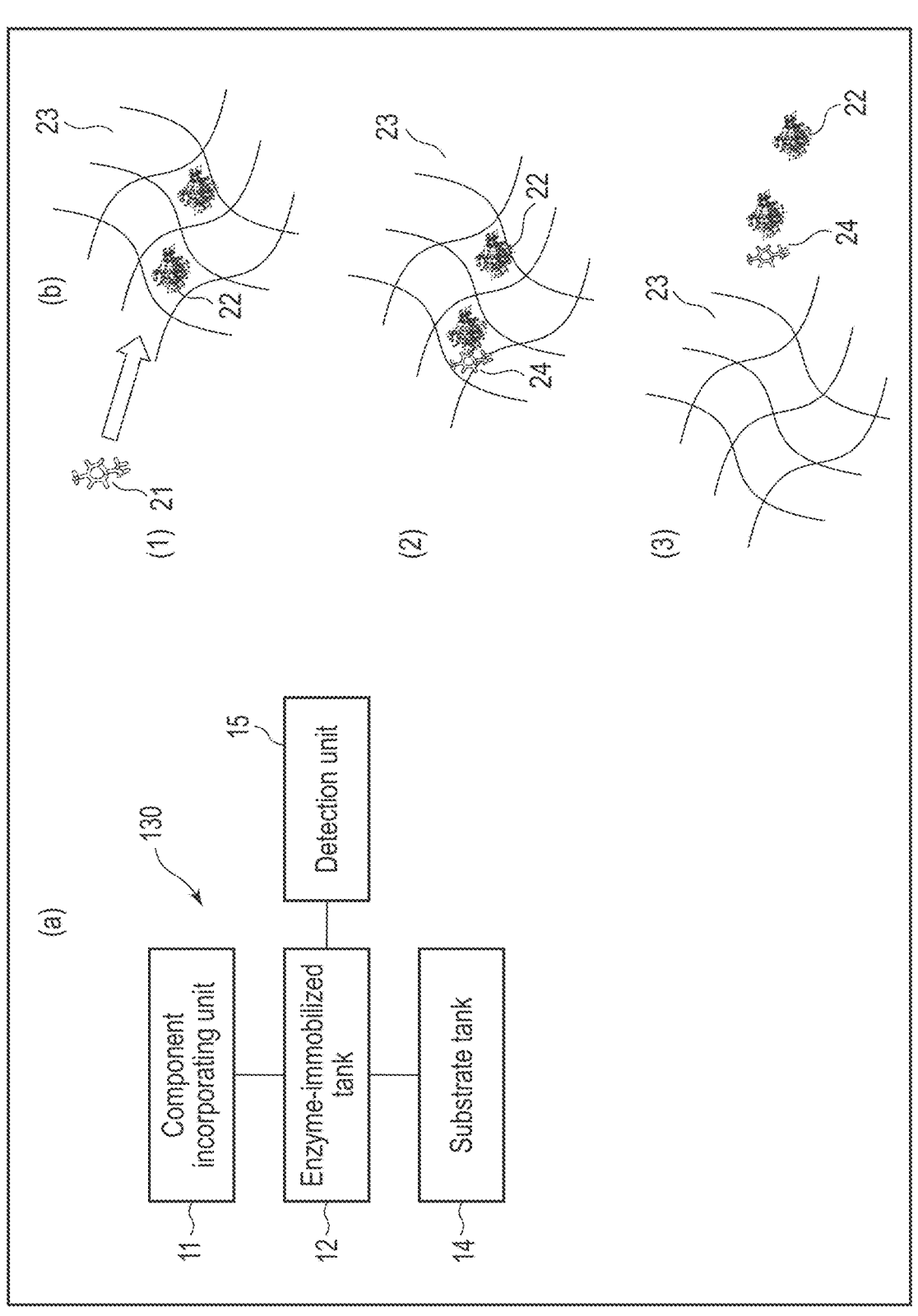
FIG. 3 is a diagram illustrating a third embodiment.

A third embodiment will be described with reference to FIG. 3. As illustrated in FIG. 3(*a*), a sensing device 130 includes a component incorporating unit 11, an enzyme-immobilized tank 12 connected to the component incorporating unit 11, a substrate tank 14 that supplies a substrate solution to the enzyme-immobilized tank 12, and a detection unit 15 that senses a reaction product generated by a reaction between an enzyme and a substrate.

In the case of the sensing device 130, an enzyme 22 is detachably immobilized on a support 23 and included in the enzyme-immobilized tank 12. A target substance 21, introduced into the sensing device 130 by incorporating the sample or at least a part of the component of the sample by the component incorporating unit 11, comes into contact with the immobilized enzyme 22 in the enzyme-immobilized tank 12 (FIG. 3(*b*)(1)) and binds to form a complex 24 (FIG. 3(*b*)(2)). Sensing by the detection unit 15 can be performed in a state where the support 23 is fixed as a sensor of the detection unit 15 (FIG. 3(*b*)(2)). In this case, the substrate solution is sent from the substrate tank 14 to the enzyme-immobilized tank 12. Alternatively, as illustrated in FIG. 3(*b*)(3), after the enzyme 22 and the complex 24 are detached from the support 23, the substrate solution may be sent to a container (not illustrated) provided in the detection unit 15, and the substrate solution may be received from the substrate tank 14 connected to the container, and the reaction and sensing may be performed.

In the absence of the substrate, by forming the complex 24 with the enzyme 22 in a low density state by being immobilized in the enzyme-immobilized tank 12, a trace amount of target substance can be detected with higher sensitivity.

Fourth Embodiment

As in a fourth embodiment illustrated in FIG. 4, any of the sensing devices described in the above embodiments and the following embodiments may further include a control unit 42 for controlling operations and functions of the component incorporating unit 11, the enzyme-immobilized tank 12, the enzyme capture tank 13, and the substrate tank 14, and movement of liquid between these elements, that is, feeding. The control unit 42 may control one element independently or may control two or more elements to be interlocked. The control unit 42 can be, for example, a computer or the like.

With such a configuration, it is possible to detect a trace amount of the target substance with higher sensitivity more easily.

Fifth Embodiment

Figure 5:
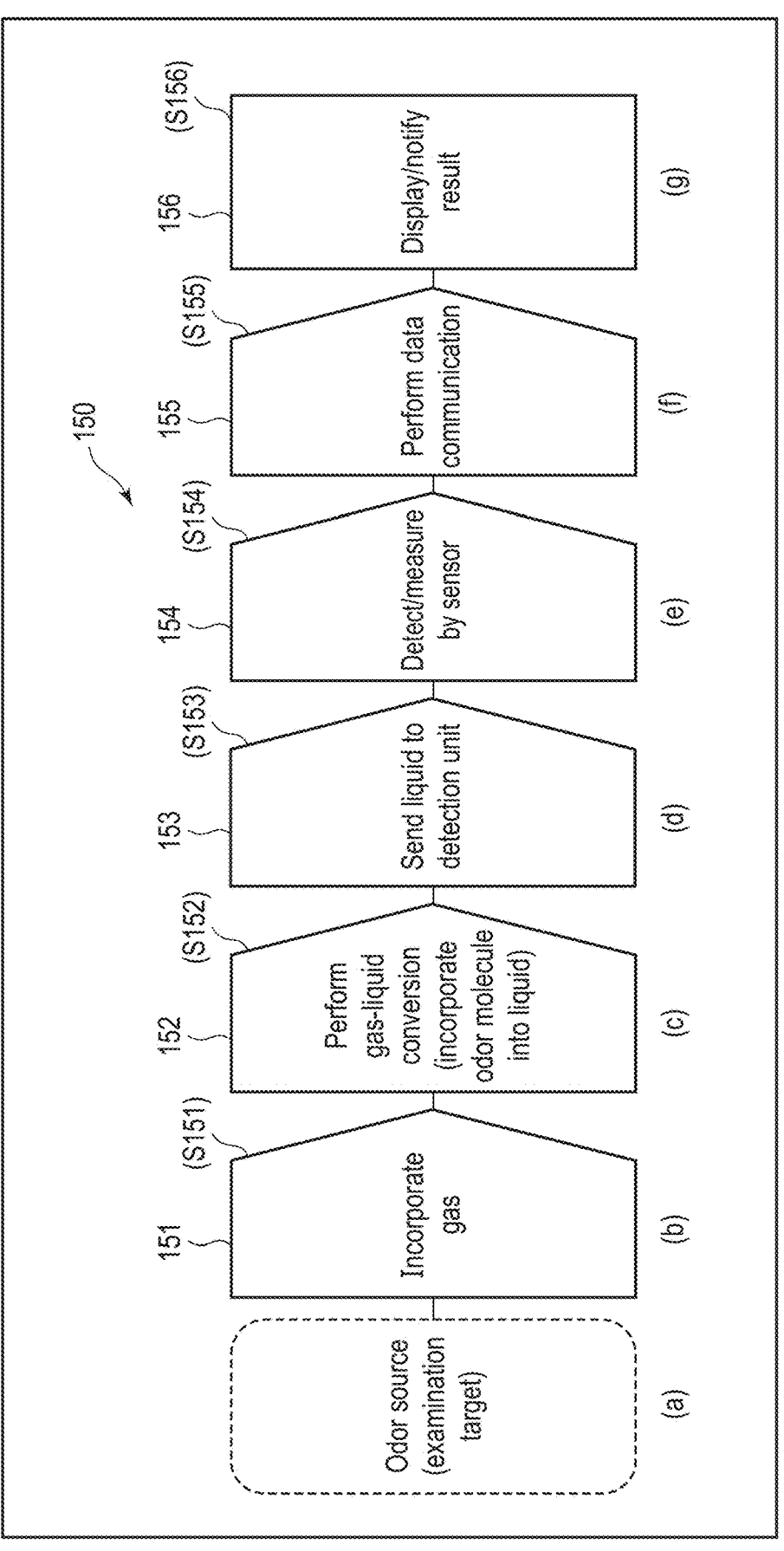
FIG. 5 is a diagram illustrating a fifth embodiment.

A configuration and an operation procedure of a sensing device 150 will be described as a fifth embodiment with reference to FIG. 5. The sensing device 150 includes a gas incorporating unit 151, a gas-liquid conversion unit 152, a liquid delivery system 153, a sensor 154, a data communication unit 155, and a result display/notification unit 156. The gas incorporating unit 151 incorporates a sample or at least a part of a component of the sample (S151). Next, the incorporated sample or component is gas-liquid converted and incorporated into a liquid (S152). The liquid including the components is sent to a detection unit by the liquid delivery system (S153). The liquid fed to the detection unit is brought into contact with the substrate after the complex of the target substance and the enzyme is formed as described above, and the reaction product generated in the contact is sensed by the sensor (S154). The sensing result is transmitted to the result display/notification unit 156 by the data communication unit 155 electrically connected to the sensor (S155). In the result display/notification unit 156 that has received the data, the result is displayed and/or notified (S156).

According to the fifth embodiment, it is possible to detect a trace amount of a target substance with higher sensitivity more easily. Such a configuration of the fifth embodiment may be combined with any sensing device described above or below. In general, many odor molecules have a molecular weight of about 100 to 200, have few functional group characteristics, and have no charge. Due to such circumstances, it is difficult to selectively detect, and in particular, since there is no charge, it is difficult to directly recognize with an electronic device. The sensing device can detect the odor molecule in such a situation more favorably.

Sixth Embodiment

Figure 6:
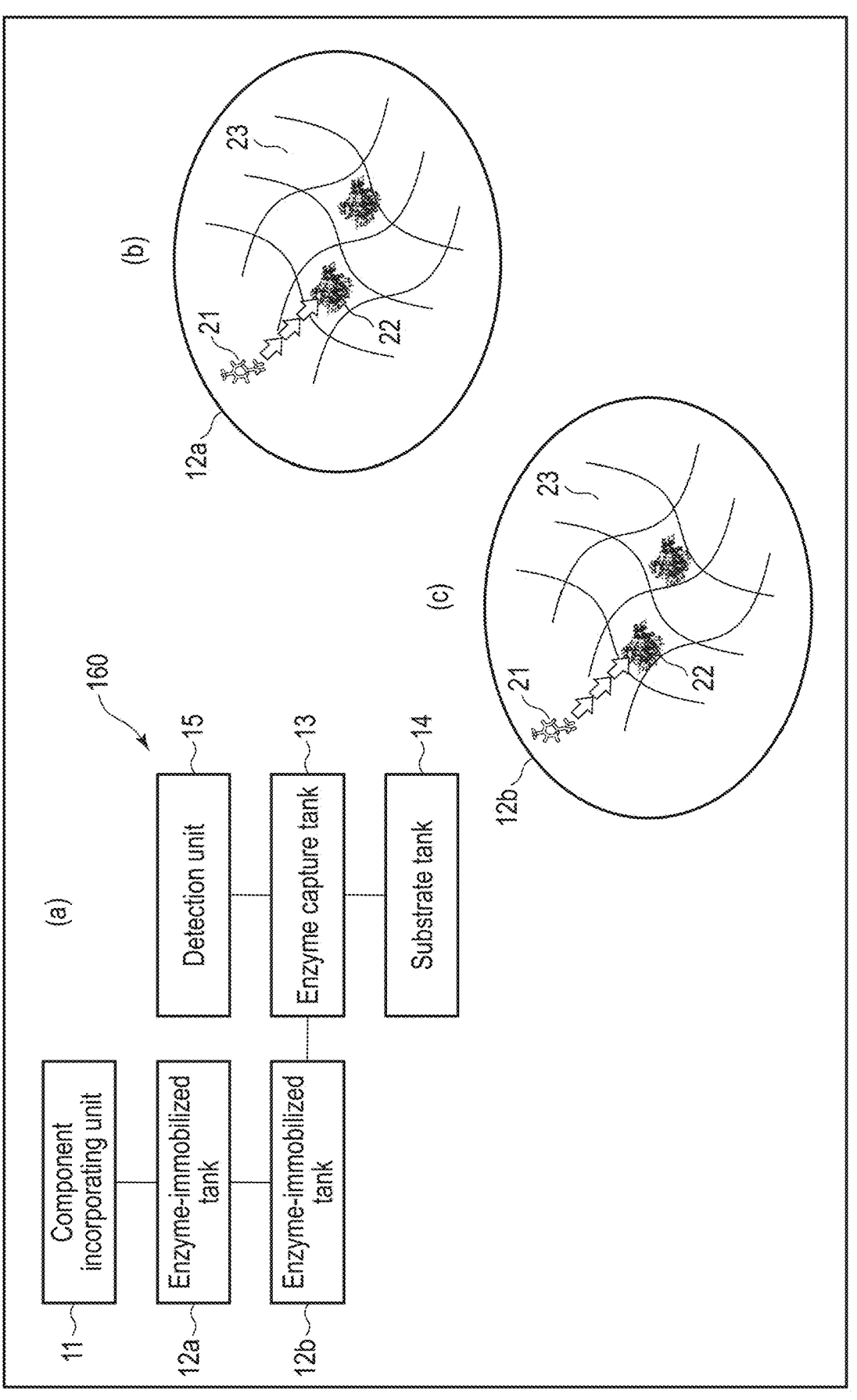
FIG. 6 is a block diagram illustrating a sixth embodiment.

A sensing device 160 according to a sixth embodiment will be described with reference to FIG. 6. The sensing device 160 includes a component incorporating unit 11, a first enzyme-immobilized tank 12A, a second enzyme-immobilized tank 12B, an enzyme capture tank 13, a substrate tank 14, and a detection unit 15. In this embodiment, by providing two enzyme-immobilized tanks connected in series, it is possible to increase the generated signal by increasing the volume since the total amount of enzyme can be doubled while maintaining the immobilized state in a state where an enzyme concentration is low. This configuration can be realized by one air/liquid feeding mechanism.

Regarding a relationship between an enzyme density and a size of an enzyme immobilization region, for example, when the enzyme density is set to $1/1000$, the size of the enzyme immobilization region simply needs to be 1000 times the volume in order to secure the magnitude of the signal. For example, in the sensing device according to the embodiment, for example, in order to immobilize the enzyme in a flow path type enzyme capture tank 13 having a length of 1 mm and a diameter of 0.6 mm to obtain a sufficient signal by the detection unit 15, and then, in order to immobilize the amount of the enzyme in one enzyme-immobilized tank 12, in the case of a device including only one enzyme-immobilized tank 12, the volume of the enzyme-immobilized tank needs to include a support that provides, for example, a cylindrical volume having a length of 10 mm and a diameter of 600 mm. This volume can also be provided by one enzyme-immobilized tank 12. However, by providing two enzyme-immobilized tanks, it is possible to reduce the volume per one or to provide a volume equal to or larger than a required size.

According to such a sixth embodiment, it is possible to detect a trace amount of a target substance with higher sensitivity more easily. Such a configuration of the sixth embodiment may be combined with any sensing device described above or below.

Seventh Embodiment

A sensing device according to a seventh embodiment will be described with reference to FIG. 7. A sensing device 170 includes a component incorporating unit 11, an enzyme-immobilized tank 12 in communication with the component incorporating unit 11, a cleaning solution tank 71 through a first valve 72A in a flow path connecting the component incorporating unit 11 and the enzyme-immobilized tank 12, a substrate tank 14 through a second valve 72B, and a detection unit 15 in communication with the enzyme-immobilized tank 12. After the target substance binds to the enzyme immobilized on the enzyme-immobilized tank 12 to form a complex, the enzyme-immobilized tank 12 may be washed with a cleaning solution from the cleaning solution tank 71, and the cleaning solution from the cleaning solution tank 71 may be provided as necessary. The first valve 72A and the second valve 72B may be, for example, valves or the like, and may be opened and closed by a control unit (not illustrated).

According to such a seventh embodiment, it is possible to detect a trace amount of a target substance with higher sensitivity more easily. Such a configuration of the seventh embodiment may be combined with any sensing device described above or below.

Eighth Embodiment

A sensing device of an eighth embodiment will be described with reference to FIG. 8. A sensing device 180 includes a component incorporating unit 11, an enzyme-immobilized tank 12 in communication with the component incorporating unit 11, an enzyme capture tank 13, a substrate tank 14 connected to a flow path connecting the enzyme-immobilized tank 12 and the enzyme capture tank 13 via a valve, and a detection unit 15 connected to the enzyme capture tank 13. By connecting the substrate tank 14 via a valve for example, it is possible to more precisely manage the flow of the substrate solution from the substrate tank 14. For example, the valve can be a manual valve.

According to such an eighth embodiment, it is possible to detect a trace amount of a target substance with higher sensitivity more easily. Such a configuration of the eighth embodiment may be combined with any sensing device described above or below.

Ninth Embodiment

A ninth embodiment is an example of a more detailed configuration of the component incorporating unit 11. Hereinafter, description will be made with reference to FIG. 9. A sensing device 190 includes a filter structure unit 90 as a gas-liquid conversion unit integrated with a component introduction unit 16, a component incorporating liquid tank 17, an enzyme-immobilized tank 12, an enzyme capture tank

13, a detection unit 15, and a substrate tank 14 (FIG. 9(a)). The configuration is basically similar to that of the first embodiment except that the filter structure unit 90 is provided. As illustrated in FIG. 9(b), the filter structure unit 90 includes a housing 91, a first flow path 93 for passing a gas with a filter 92 interposed in the housing, and a second flow path 94 for passing an incorporating liquid from the incorporating liquid tank 17. By allowing the gaseous sample to flow into the first flow path 93, the sample or at least a part of a component of the sample passes through the filter 92 and is incorporated into the incorporating liquid from the incorporating liquid tank 17.

According to such a ninth embodiment, it is possible to efficiently incorporate a gaseous sample or at least a part of a component thereof into the sensing device, and it is possible to detect a trace amount of a target substance with higher sensitivity more easily.

Tenth Embodiment

Figure 10:
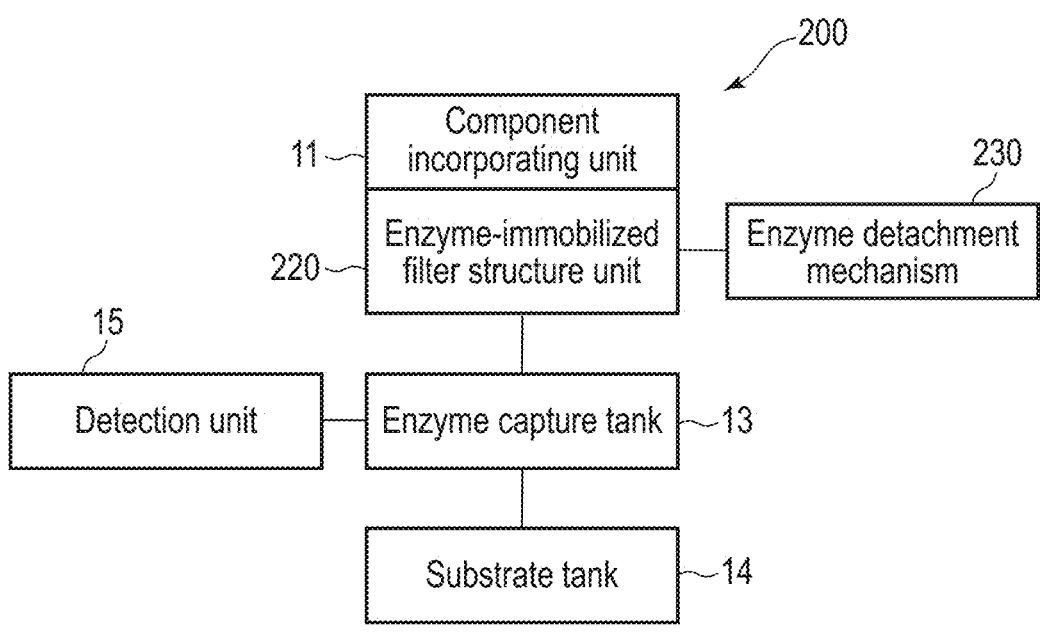
FIG. 10 is a block diagram illustrating a tenth embodiment.

A tenth embodiment is characterized in that an enzyme is immobilized on the filter structure unit 90 of the ninth embodiment. This makes it possible to promote binding between a target substance and an immobilized enzyme and form a complex while incorporating a sample into a component incorporating liquid by gas-liquid exchange. A sensing device 200 includes a component incorporating unit 11, an enzyme-immobilized filter structure unit 220 including a filter to which an enzyme is detachably immobilized, an enzyme detachment mechanism 230, an enzyme capture tank 13, a detection unit 15, and a substrate tank 14 (FIG. 10). It can be interpreted that the component incorporating unit 11 and the enzyme-immobilized tank are integrated. The component incorporating unit 11 includes a gas introduction port 16, the enzyme-immobilized filter structure unit 220 in which an enzyme is immobilized on a filter portion of a filter structure unit 90 (see FIG. 9(b)) as a gas-liquid conversion unit, and a component incorporating liquid tank 17. By using the enzyme-immobilized filter structure unit 220, it is possible to widen the enzyme immobilization region. In addition, since the distance to the gas phase is short, it is possible to incorporate more target substance molecules contained in the sample.

For example, assuming that a nonwoven fabric of 1 cm×1 cm is immobilized in the flow path and an amount of enzyme capable of obtaining a sufficient signal is specified, when the same amount of enzyme is to be immobilized in the enzyme-immobilized tank at the same density as that at this time, the enzyme density is desired to be 1/1000. Therefore, a volume of 1000 times is simply required, and when the enzyme-immobilized filter structure unit 220 is to realize the volume, the size is 30 cm×30 cm or more. However, even such a size is a size within a range that can be sufficiently achieved.

According to the tenth embodiment as described above, it is possible to efficiently incorporate a gaseous sample or at least a part of a component thereof into the sensing device, and it is possible to detect a trace amount of a target substance with higher sensitivity more easily.

Eleventh Embodiment

As an eleventh embodiment, an example of an enzyme detachment mechanism for detaching an immobilized enzyme will be described. An example illustrated in FIG. 11 illustrates an example of an enzyme detachment mechanism for performing detachment by heating from a state in which an enzyme 22 is immobilized on a support in an enzyme-immobilized tank 12. For example, in this enzyme detachment mechanism, a nucleic acid molecule such as DNA is used to immobilize the enzyme. The support is illustrated as an immobilized base material 1120. A surface modification 1121 known per se such as a thiol group is applied to a surface of the base material 1120, and an anchor 1130 for immobilization is immobilized on the surface modification. Meanwhile, a flag 1110 having a sequence complementary to a sequence of the anchor 1130 is assigned to the enzyme 22. Thereby, the immobilization of the enzyme 22 on the immobilized base material 1120, that is, the support, is achieved by the bonding resulting from the complementarity between the anchor 1130 and the flag 1110. The immobilized enzyme can be easily detached by heating to TM or more, and can flow downstream.

Since the TM value can be changed by adjusting the nucleic acid sequence to be used, for example, complementary strand DNA may be designed so as to be separated at a temperature range for retaining enzyme activity, for example, about 30 to 60° C. When such a nucleic acid is used, for example, a DNA having a complementary strand sequence of 10 bases or less may be used. As a material of the immobilized base material 1120, it is preferable to use paper, for example, a nonwoven fabric or a cellulose material, particles, for example, gold nanoparticles or polymer particles, or a porous structure, for example, porous glass or ceramics.

Twelfth Embodiment

As a twelfth embodiment, a further example of an enzyme detachment mechanism for detaching an immobilized enzyme will be described. An example illustrated in FIG. 12 is a mechanism in which an electrochemical reaction of chemical modification is applied from a state in which an enzyme 22 is immobilized on a support in an enzyme-immobilized tank 12. A surface of an immobilized base material 1122 as a support is modified with, for example, gold to achieve binding to a thiol group on the enzyme side. In this mechanism, for example, an electrode 1121 of a counter electrode such as AG/AGCL is disposed together with the immobilized base material 1122. When the enzyme 22 is detached, a potential difference of about −1 V is generated, so that the enzyme can be detached by an electrochemical reaction and flow downstream. In addition to using an electrochemical reaction, a photodegradable molecular probe, a PH-degradable probe, and the like can also be used as a linker for immobilizing the enzyme 22 and the immobilized base material 1122 (not illustrated).

Thirteenth Embodiment

As a thirteenth embodiment, a further example of an enzyme detachment mechanism for detaching an immobilized enzyme will be described. An example illustrated in FIG. 13 is a mechanism in which a support itself or a part of the support, which has the enzyme 22 immobilized in an enzyme-immobilized tank 12, disappears depending on conditions to lead the enzyme 22 detached from the support. The mechanism is characterized by utilizing decomposability and functionality of a material constituting the support. In this case, examples of the material of the support include a photosensitive polymer or a gel. Depending on decomposition properties of the material of the selected support, it is possible to decompose the support, for example by thermal decomposition, electrochemical reaction decomposition, photolysis or the like, thereby detaching the enzyme. In addition, by using a functional polymer as the support material, it is also possible to detach the enzyme by a mechanism) such as structural change and swelling, in addition to the above-described degradation.

Fourteenth Embodiment

As a fourteenth embodiment, an example of a mechanism for capturing an enzyme and an enzyme-target substance complex in an enzyme capture tank 13 is illustrated in FIG. 14. In the enzyme capture tank 13, it is desirable to capture an enzyme 22 and a complex 24 from the upstream at a higher density. For this purpose, for example, a nucleic acid such as DNA can be used. The enzyme 22 is provided with a DNA fragment as a flag 1110 to prepare a flagged enzyme 1111. A capture unit 25 of the enzyme capture tank 13 can use the material and configuration used as a support in an enzyme-immobilized tank 12. Details are as described in the above-described eleventh embodiment.

Fifteenth Embodiment

As a fifteenth embodiment, a further example of a mechanism for capturing an enzyme and an enzyme-target substance complex in an enzyme capture tank 13 is illustrated in FIG. 15. Examples thereof include a mechanism using a chemical reaction and a mechanism using a magnetic body. In the case of using a chemical reaction, for example, by modifying a capture unit 25 with an amino group such as $NH_2$ in advance, an enzyme 22 and a complex 24 can be captured at a higher density. The immobilization is performed by a reaction between a hydroxyl group of an enzyme and an amino group. It is possible to utilize not only $NH_2$ but also a bond modification for immobilizing common proteins such as —SH, —COOH, and —CHO. In addition, the base material may be, for example, paper, for example, a nonwoven fabric or a cellulose material, particles, for example, gold nanoparticles or polymer particles, or a porous structure, for example, porous glass or ceramics.

In the case of a mechanism using a magnetic body, for example, an enzyme is immobilized on magnetic beads, and a material for binding the magnetic beads, such as iron or a magnet, is selected and used as the capture unit 25, whereby the enzyme and the complex from the upstream can be efficiently captured at high density. However, the capturing mechanism that can be used is not limited thereto.

Sixteenth Embodiment

A sixteenth embodiment is a method for detecting a target substance. The method includes incorporating a gaseous sample into a liquid by gas-liquid conversion, binding the liquid to a target substance and bringing the liquid into contact with an enzyme immobilized on a support to form a complex of the target substance and the enzyme, and thereafter, bringing a substrate into contact with the enzyme to detect a change in activity of the enzyme based on an inhibitory effect, due to presence of the target substance, on a reference signal generated between the enzyme in which the complex is not formed and the substrate.

As described above, that is, by efficiently generating an enzyme-target substance complex in a state where an enzyme concentration and a substrate concentration are low, high sensitivity can be realized. Such a method may be carried out with a device according to embodiments.

Seventeenth Embodiment

A reference signal acquisition method will be described as a seventeenth embodiment. When a sensing device is used, a basic operation of the method is (1) complex formation between a detection target and an enzyme in an enzyme-immobilized tank and (2) detachment of an enzyme-enzyme inhibitor complex, and (3) high-density enzyme capture in an enzyme capture tank 13 and (4) enzyme activity evaluation by substrate feeding. In this evaluation, it is necessary to compare the concentration with a concentration of a reaction product when a target substance such as an odor molecule is not present. The acquisition of a reference signal as a control, in which the target substance is not present, may be referenced by actually performing a detection procedure on the control sample in advance, for example, when the concentration and activity of the enzyme are stable, or a calibration curve may be prepared each time the detection is performed.

Alternatively, the reference signal can be obtained by performing the measurement under the same conditions as when the sample is measured except that the target substance is not present. Alternatively, the measurement may be performed using an element adjusted to achieve an enzyme activity rate under targeted detection conditions, or the measurement may be performed using an element adjusted to achieve an enzyme activity rate of a targeted lower detection limit. These three reference signal acquisition methods may be comprehensively used as a reference signal used for one detection, or any one or two may be selected and used as a reference signal.

A basic operation actually performed to obtain the reference signal is as follows. That is, the following operations (1) to (5) may be repeated. First, in the enzyme-immobilized tank 12, (1) complex formation between the detection target and the enzyme and (2) detachment of the enzyme/enzyme inhibitor complex, and subsequently, in the enzyme capture tank 13, (3) high-density enzyme capture, (4) enzyme activity evaluation by substrate feeding, and (5) detachment of the enzyme-enzyme inhibitor complex may be repeated.

By acquiring the reference signal in this manner, more accurate detection can be performed.

Eighteenth Embodiment

An eighteenth embodiment describes a method for detecting a target substance in a sample using the sensor of the first embodiment. The detection method includes, for example, a step of incorporating a sample, a step of converting presence or absence and an amount of a sample into a signal, and a determination step of detecting the signal and determining the presence or absence or concentration of a target substance in the sample. Hereinafter, an example of each step will be described with reference to FIGS. 1A and 1B.

First, as a step of incorporating a sample, the sample is incorporated into a solution. Next, the solution containing the incorporated sample is conveyed to a signal conversion unit, and the amount of the sample is converted into a signal. As a conversion method, detection target concentration dependence of a decomposition rate of a substrate by the enzyme is used, and for example, the conversion is performed by increasing or decreasing a production amount of byproduct. Here, using an enzyme whose detection target is an inhibitor, a state in which the activity of the enzyme decreases depending on the presence or absence and concentration of the detection target is detected as a decrease in the decomposition rate of the substrate. For example, as an example, a system is possible in which limonene is used as a detection target, acetylcholinesterase is used as an enzyme, acetylcholine is used as a substrate, and an increase or decrease in the amount of protons of a product is used as a physical quantity to be sensed.

In this embodiment, a sensor including an enzyme-immobilized tank 12 and an enzyme capture tank 13 is proposed as a signal conversion unit. The enzyme-immobilized tank 12 is a tank having a function of immobilizing and releasing the enzyme, and the enzyme capture tank 13 is a tank having a function of immobilizing the enzyme conveyed from the enzyme-immobilized tank 12 although there is no enzyme at a measurement start time point. First, a solution conveyed from a component incorporating unit is conveyed to the enzyme-immobilized tank 12. Here, by lowering the enzyme concentration in the enzyme-immobilized tank 12, it is possible to bind to a detection target with a low concentration with a high probability. Next, after feeding the incorporating solution, the enzyme is detached from the enzyme-immobilized tank 12. Furthermore, a mechanism can be provided which individually or collectively controls conveyance of a liquid incorporating the sample or at least a part of a component thereof, application of a signal to the enzyme-immobilized tank 12, conveyance of the substrate liquid, application of a signal to the enzyme capture tank 13, and operation of the sensor. Such a mechanism may be pumping or drawing of a liquid phase by a pump.

As the detachment method, other actions such as heat, electricity, and magnetism can be used. For example, DNA can be used as a mechanism of thermal detachment. DNA is known to undergo double strand formation or single strand detachment at a temperature of about 40 to 90° C. depending on the chain length and sequence thereof. DNA of one side is modified to a base material, and DNA of the other side is modified to an enzyme, so that a double strand is formed at a double strand forming temperature or less, and the enzyme is captured in the base material. By setting the temperature to be equal to or higher than the double strand forming temperature after feeding the detection liquid, separation can be easily performed, and the enzyme can be detached. By such a method, the enzyme is detached from the enzyme-immobilized tank at an arbitrary timing. The detachment method is not limited to thermal separation using the DNA, and various methods such as application of electrochemical reaction and immobilization with a photosensitive polymer can be used.

Next, the enzyme and the like are conveyed to the enzyme capture tank 13, and at least the enzyme is captured and immobilized in the enzyme capture tank 13. Here, immobilization at a high density makes it possible to increase the rate of production of a product by an enzymatic reaction and to maintain a high signal. Here, double strand formation of the DNA can be used as the capture tank 13. Specifically, DNA to be a complementary strand of single-stranded DNA modified with the enzyme is immobilized, and the enzyme can be immobilized in the capture tank via double strand formation of DNA by carrying the DNA in an environment at a double strand forming temperature or lower. Here, the capturing method can be realized not only by a method using temperature but also by a method using the illustrated chemical reaction, a method using magnetism, or another method.

The material to be the sample is not limited to a gas sample, but is, for example, air, exhalation, or another gas generated from an analysis target such as a living body or an object, or air around the analysis target. The target substance in the gas sample, that is, the target substance is not limited, but is, for example, a volatile organic compound (VOC) such as an odor substance or a pheromone substance.

Specifically, in addition to limonene, terpenoids such as ambreine and pinene, polyphenols typified by flavonoid such as luteolin, alkaloids such as galantamine, and glycosides such as CYNATROSIDE A, and also components of drugs acting on the neurotransmission system, such as phenylethylamine and cocaine can be targets.

Next, the detection unit measures, for example, the pH of the solution, and determines the concentration of the detection target from the change of the pH, and so. By such a method, it is possible to detect a trace amount of a target substance with higher sensitivity more easily.

Nineteenth Embodiment

Figure 16:
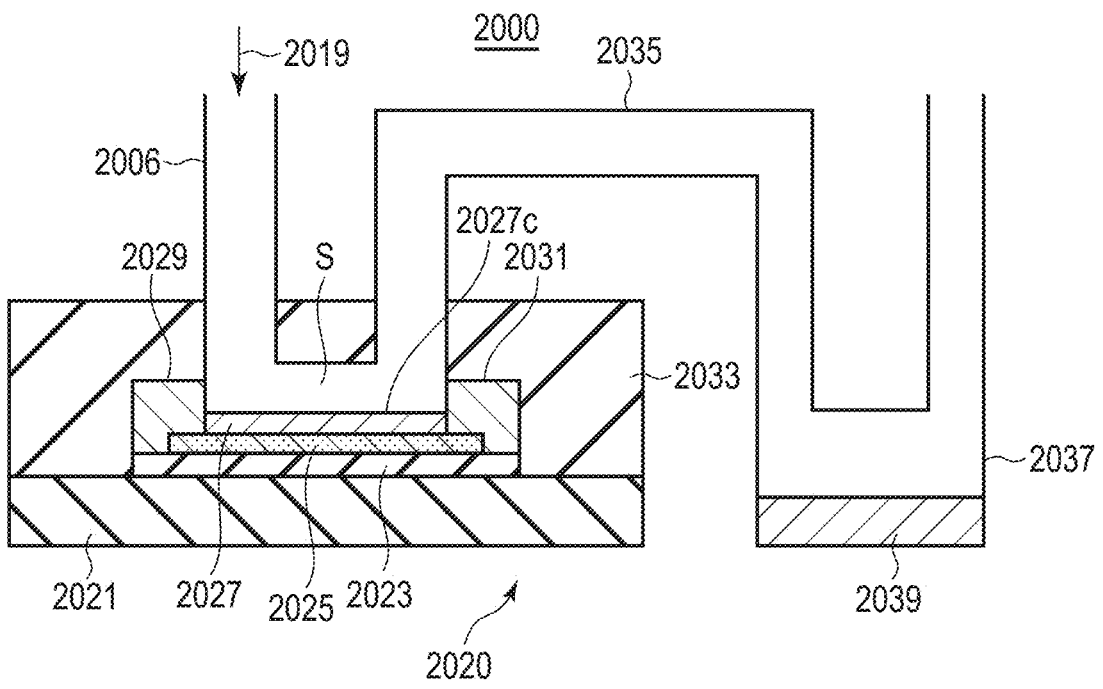
FIG. 16 is a schematic diagram illustrating a sixteenth embodiment.

A structure of a detection unit 15 as a sensor in the sensing device according to the above-described first embodiment will be described in detail with reference to FIG. 16.

For example, the detection unit 15 may have a configuration of a graphene field effect transistor (graphene FET) in a case where a change in proton concentration is detected as a signal. The sensor is not limited to the graphene FET, and may have a configuration of another charge detection element, ISFET, CCD, PH meter, glass electrode, or the like, for example. In addition, a sensor that detects an increase or decrease in hydrogen peroxide or the like may be used depending on the enzyme used for a signal conversion unit. As the sensor that detects the increase or decrease of hydrogen peroxide, a sensor that detects a response current such as cyclic voltammetry can be used.

A detection unit 2000 includes a sensing element 2020 and an electrode tank 2037. The sensing element 2020 detects a product amount or a substrate amount. The sensing element 2020 includes, for example, a graphene field effect transistor (graphene FET). That is, the graphene FET includes a substrate 2021, an insulating film 2023 disposed on a surface of the substrate 2021, a graphene sensitive membrane 2025 disposed on the insulating film 20, a probe 2027 that binds to a product or a substrate disposed on the sensitive membrane 2025, a source electrode 2029 connected to one end of the sensitive membrane 2025, a drain electrode 2031 connected to the other end of the sensitive membrane 2025, and a protective film 2033 covering the substrate 2021 including the source electrode 2029 and the drain electrode 2031. The sensing element 2020 may be configured not to include the probe 2027. In the protective film 2033, a space S having a rectangular shape is provided above a principal surface 2027C of the sensitive membrane 2027, and the principal surface 2027C is exposed to the space S. The space S on the source electrode 2029 side is connected to a conduit 2006 on the enzyme capture tank 13 and/or the enzyme-immobilized tank 12 side. The conduit 2006 communicates with the enzyme-immobilized tank 12 when the enzymatic reaction with the substrate is performed in the enzyme capture tank 13, and communicates with the enzyme capture tank 13 when the enzymatic reaction is performed in a reaction container (not illustrated) provided inside the previous detection unit 15 sent from the enzyme capture tank. The space S on the drain electrode 2031 side is connected to a conduit 2035, and the electrode tank 2037 is formed on the way of the conduit 2035. A gate electrode 2039 is disposed in the electrode tank 2037. Note that a solution 2019 that has passed through the reaction field is sent into the space S through the conduit 2006 as indicated by an arrow, is brought into contact with the principal surface 2027C of the sensitive membrane 2027, then passes through the conduit 2035, passes through the electrode tank

2037, is brought into contact with the gate electrode 2039 in the electrode tank 2037, and is discharged to the outside.

The substrate 2021 has, for example, a rectangular plate shape. The material of the substrate 2021 is, for example, silicon, glass (SIO or the like), ceramics (SIN or the like), a polymer material, or the like. The substrate 2021 may have a laminated structure in which an insulator layer is provided on an electric body layer. The size of the substrate 2021 is not limited, but for example, the thickness of the substrate 2021 can be about 1 mm. The length and the width may be selected so as to have a desired size according to the application of the sensing device 1.

The sensitive membrane 2027 is a pH detection element, and is, for example, an ion sensitive membrane made of a metal oxide film such as $SIO_2$, SIN, $AL_2O_3$, or $TA_2O_3$. However, the sensitive membrane 2027 is not limited to the pH detection element, and other elements that detect a change in physical properties due to binding or proximity between the enzyme to be used and the substrate or the reaction product thereof may be adopted. As a material constituting another element, for example, a carbon material in the form of graphene, diamond, or carbon nanotube, a layered compound such as molybdenum disulfide ($MOS_2$) or tungsten diselenide ($WSE_2$), titanium disulfide ($TIS_2$), or phosphorus (P), or a material electrochemically safe in an oxidation-reduction region of water such as gold (Au), platinum (Pt), or silver (Ag) can be used. The sensitive membranes 2027 may be, for example, at least one atomic layer, but may be multiple. Alternatively, the sensitive membranes 2027 may have the shape of nanowires or nanotubes.

A desired length can be selected for the dimension of sensitive membranes 2027 according to the application, but the length from one end on the source electrode 2029 side to the drain electrode 2031 side is preferably, for example, 10 nm to 1 mm. Here, assuming that a direction from the source electrode 2029 side toward the drain electrode 2031 side is a first direction, a direction which is orthogonal to the first direction and in which the detection unit 2000 is viewed in cross section is a second direction, it is preferable that the sensitive membrane 2027 is formed such that a length of the principal surface 2027C in the second direction is longer than a length of the rectangular shaped space S above the sensitive membrane 2027 in the second direction, or a length of the space S in the second direction is equal to a length of the principal surface 2027C in the second direction. Such a configuration can increase a ratio of a laminated portion of the sensitive membrane/channel portion in contact with the solution in the second direction, and can improve the detection sensitivity.

The sensor can be manufactured by a semiconductor process. For example, the graphene FET sensor can be manufactured as follows.

First, an insulating film 20 for preventing discharge is formed on the substrate 2021. When the substrate 2021 itself has an insulating property, it may be omitted.

Next, a sensing element including a channel, a first electrode, a second electrode, here, the source electrode 2029 and the drain electrode 2031, and the protective film 2033 is formed on the substrate 2021. An example of using a graphene FET as the sensing element will be described below.

First, graphene is formed on the substrate (wafer) 2021. As a method for forming graphene, transfer from graphite or a CVD method can be used. In the case of using transfer or the like, graphene on which a pattern is formed by a printing technique or the like may be bonded. Thereafter, the graphene is patterned. At this time, a resist, a mask, or the like formed at the time of patterning may remain on the graphene. In addition, a base for forming graphene may be patterned in advance, and then graphene may be selectively formed by, for example, a CVD method or the like.

After the graphene is formed, a first electrode and a second electrode are formed at both ends of the graphene. A probe 2027 such as a protein nucleic acid aptamer is formed. When the proton concentration is detected, an oxide film such as $TA_2O_5$ may be formed. Next, a protective film is formed. The protective film may be processed into a target shape using lithography or patterning, or may be formed by lift-off or the like using a sacrificial layer or the like. At the time of forming the protective film, an opening is formed so as to satisfy the above conditions. Finally, a space S such as a flow path is formed.

The sensor further includes, for example, a circuit (not illustrated) including a power supply that applies a voltage between the first electrode and the second electrode, and an ammeter that measures a value of a current flowing between the first electrode and the second electrode. These can be provided, for example, in the substrate 2021. In addition, the sensor may include a pad connected to the first electrode and the second electrode (not illustrated).

One sensing element including one channel, one first electrode, one second electrode, and one opening may be disposed on one substrate 2021, or a plurality of sensing elements may be disposed. Furthermore, this is an example of a sensing element, and other elements may be used.

By using the detection unit as such a sensor, it is possible to detect a trace amount of target substance with higher sensitivity more easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A sensing device comprising:

a gas sampler that incorporates a gaseous sample or a part of a component of the sample into a liquid by causing the sample to pass through a filter structure to perform gas-liquid conversion, the filter structure having an enzyme detachably immobilized thereon, activity of the enzyme being inhibited by binding of a target substance;

an enzyme capture tank that captures an enzyme detached from the filter structure and a complex of the target substance and the enzyme detached from the filter structure;

a substrate tank that supplies a substrate solution to the enzyme capture tank; and a sensor that performs sensing of an amount of a substrate or an amount of a product contained in the substrate solution supplied to the enzyme capture tank.

2. The sensing device of claim 1, wherein the sensing is to detect a change in enzyme activity of the enzyme detached from the filter structure based on enzyme inhibition due to specific and reversible binding to the enzyme by a target substance contained in the sample.

3. The sensing device of claim 1, wherein the gas sampler further comprises a sample introduction port that receives the sample and sends the sample to the filter structure, and a component incorporating liquid tank that accommodates a liquid sent to the filter structure to incorporate the sample or a part of the sample therein.

4. The sensing device of claim 1, wherein the gas sampler further comprises an enzyme detachment mechanism that detaches the enzyme immobilized on the filter and a complex of the enzyme and a detection target, and the enzyme detachment mechanism is a heater, electrodes, or a pH adjuster.

5. The sensing device of any one of claim 1 to claim 4, further comprising a controller that controls a function of the gas sampler, the enzyme capture tank, and the substrate tank.

6. The sensing device of any one of claim 1 to claim 4, further comprising a mechanism that individually or collectively controls (a) conveyance of the liquid incorporating the sample or at least a part of a component of the sample, (b) application of a signal to an enzyme-immobilized tank, (c) conveyance of a substrate liquid, (d) application of a signal to the enzyme capture tank, and (e) operation of the sensor.

7. The sensing device of any one of claim 1 to claim 4, wherein inhibition of enzyme activity by the target substance is inhibition due to an inhibitory action.

* * * * *